United States Patent [19]

Sato et al.

[11] 4,367,230

[45] Jan. 4, 1983

[54] NOVEL TRIAZAFLUORANTHENE COMPOUND AND PROCESSES FOR PREPARING THE SAME

[75] Inventors: Yasuhiko Sato, Urawa; Tomishige Mizoguchi, Wako; Yukitsuka Kudo, Osaka; Ryuichi Ishida, Suita, all of Japan

[73] Assignee: Tanabe Seiyaku Co., Ltd., Japan

[21] Appl. No.: 215,107

[22] Filed: Dec. 10, 1980

[30] Foreign Application Priority Data

Jan. 4, 1980 [GB] United Kingdom ............... 8000233

[51] Int. Cl.³ ................... A61K 31/505; C07D 471/16
[52] U.S. Cl. ...................................... 424/251; 544/247
[58] Field of Search ......................... 544/247; 424/251

[56] References Cited

U.S. PATENT DOCUMENTS

4,190,657  2/1980  Koletar et al. ...................... 424/256
4,218,453  8/1980  Hannart ............................... 424/256
4,277,476  7/1981  DuPont et al. ...................... 424/250

FOREIGN PATENT DOCUMENTS

8249  2/1980  European Pat. Off. ............ 424/256

OTHER PUBLICATIONS

McOmie, Protective Groups in Organic Chemistry, Plenum Press, London and New York, (1973), pp. 62–63, 104–106 relied upon.
Laronze et al., Bull. Soc. Chim. France, 1977, No. 11–12, pp. 1207–1214.
Ordzhonikidze, S., Chemical Abstracts, vol. 84, 31133j, (1976).

*Primary Examiner*—Donald G. Daus
*Assistant Examiner*—Diana G. Rivers
*Attorney, Agent, or Firm*—Jordan B. Bierman; Linda Bierman

[57] ABSTRACT

A triazafluoranthene compound of the formula:

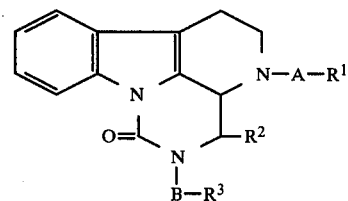

wherein $R^1$ is hydrogen, phenyl, cycloalkyl having 3 to 6 carbon atom, (lower alkoxy)carbonyl, lower alkoxy or (lower alkyl)carbonyl, $R^2$ is hydrogen or lower alkyl, $R^3$ is hydrogen, phenyl, (lower alkoxy)carbonyl, lower alkoxy, di(lower alkyl)amino, (tetrahydropyran-2-yl)oxy, hydroxy or carboxyl, A is single bond, alkylene having one to 5 carbon atoms or alkenylene having 2 to 5 carbon atoms, and B is single bond or alkylene having one to 5 carbon atoms. Methods of preparing the compound (I) are disclosed. The compound (I) and a pharmaceutically acceptable acid addition salt thereof have a potent anti-anoxic activity.

15 Claims, No Drawings

NOVEL TRIAZAFLUORANTHENE COMPOUND AND PROCESSES FOR PREPARING THE SAME

This invention relates to a novel triazafluoranthene compound and processes for preparing the same. More particularly, it relates to a 1-oxo-1H-2,3,3a,4,5,6-hexahydro-2,4,10b-triazafluoranthene compound of the formula:

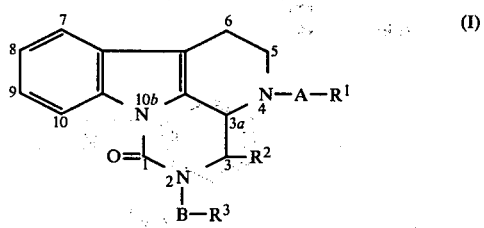

wherein $R^1$ is hydrogen, phenyl, cycloalkyl having 3 to 6 carbon atoms, (lower alkoxy)carbonyl, lower alkoxy or (lower alkyl)carbonyl, $R^2$ is hydrogen or lower alkyl, $R^3$ is hydrogen, phenyl, (lower alkoxy)carbonyl, lower alkoxy, di(lower alkyl)amino, (tetrahydropyran-2-yl)oxy, hydroxy or carboxyl, A is single bond, alkylene having one to 5 carbon atoms or alkenylene having 2 to 5 carbon atoms, and B is single bond or alkylene having one to 5 carbon atoms, or a pharmaceutically acceptable acid addition salt thereof.

Bulletin de la societe Chimique de France 1977(No. 11-12), pages 1207-1214 discloses that 1,2,3,4,5,6-octahydro-3-methyl-4-ethyl-7-oxo-azepino[1,2,3-lm]-β-carboline is prepared by intramolecular cyclization of 1,2,3,4-tetrahydro-1-(1-ethyl-3-methoxycarbonyl-propyl)-2-methyl-β-carboline. However, said literature makes no mention of a therapeutic effect of the above-mentioned azepino[1,2,3-lm]-β-carboline compound.

As a result of various investigations, we have now found that the compound (I) of the present invention and a pharmaceutically acceptable acid addition salt thereof have a potent anti-anoxic activity and are useful to enhance oxygenation of tissues, especially brain oxygenation. For example, when the effect of each test compounds upon the survival time of mice was estimated by keeping the mice (body weight: about 20 g) under reduced oxygen tension (atmospheric pressure: 165 mm Hg) 15 minutes after intraperitoneal administration thereof, $SD_{50}$ (i.e., the dose required to produce 50% increase in the survival time of mice as compared with that of a group of nonmedicated mice) of 1-oxo-1H-2,3,3a,4,5,6-hexahydro-2,4,10b-triazafluoranthene hydrochloride, 1-oxo-2-methyl-4-n-butyl-1H-2,3,3a,4,5,6-hexahydro-2,4,10b-triazafluoranthene hydrochloride and 1-oxo-2-benzyl-4-ethyl-1H-2,3,3a,4,5,6-hexahydro-2,4,10b-triazafluoranthene hydrochloride were 9.5, 39.4 and 24.8 mg/kg, respectively. Moreover, the toxicity of the compound (I) is low. For example, when administered intraperitoneally to mice, the 50% lethal dose (estimated from the number of mice died within 7 days after the administration) of 1-oxo-2-methyl-4-n-butyl-1H-2,3,3,a,4,5,6-hexahydro-2,4,10b-triazafluoranthene hydrochloride and 1-oxo-2-benzyl-4-ethyl-1H-2,3,3a,4,5,6-hexahydro-2,4,10b-triazafluoranthene hydrochloride were more than 1000 mg/kg.

Among of the compounds of the present invention, a preferred group of compounds are those of the formula (I) in which $R^1$ is hydrogen, phenyl or cycloalkyl having 3 to 6 carbon atoms, $R^2$ is hydrogen or alkyl having one to 4 carbon atoms, $R^3$ is hydrogen, phenyl or alkoxy having one to 4 carbon atoms, A is single bond or alkylene having one to 5 carbon atoms, and B is single bond or alkylene having one to 5 carbon atoms. Another preferred group of compounds are those of the formula (I) in which $R^1$ is hydrogen, phenyl or cyclohexyl, $R^2$ is hydrogen or methyl, $R^3$ is hydrogen, phenyl or ethoxy, A is single bond or alkylene having one to 5 carbon atoms, and B is single bond or alkylene having one to 5 carbon atoms. Other preferred group of compounds are those of the formula (I) in which $R^1$ is hydrogen, $R^2$ is hydrogen, $R^3$ is hydrogen, A is alkylene having one to 5 carbon atoms, and B is single bond or methylene. Other preferred group of compounds are those of the formula (I) in which $R^1$ is hydrogen, $R^2$ is hydrogen or methyl, $R^3$ is hydrogen, A is alkylene having 4 or 5 carbon atoms, and B is alkylene having one to 5 carbon atoms. Still other group of preferred compounds are those of the formula (I) in which $R^1$ is cyclohexyl or phenyl, $R^2$ is hydrogen or methyl, $R^3$ is hydrogen, A is methylene or ethylene, and B is methylene.

According to the present invention, the compound (I) can be prepared by any one of the methods (A) through (I) described in the following schemes.

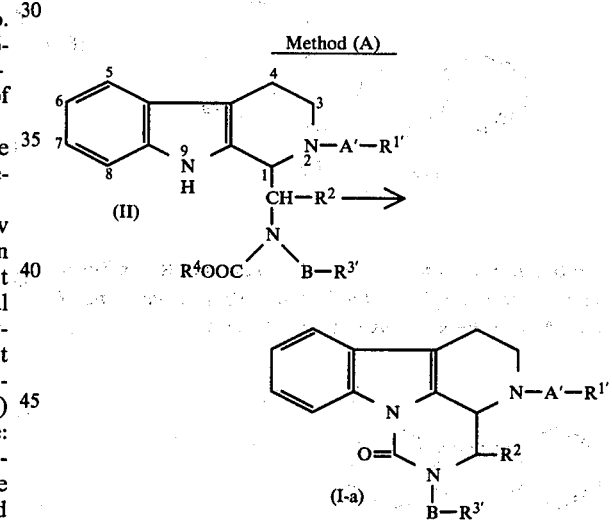

(In the above-mentioned reaction scheme, $R^{1'}$ is hydrogen, phenyl or cycloalkyl having 3 to 6 carbon atoms, $R^{3'}$ is hydrogen, $R^4$ is lower alkyl or benzyl, A' is alkylene having one to 5 carbon atoms, and $R^2$ and B are the same as defined above.)

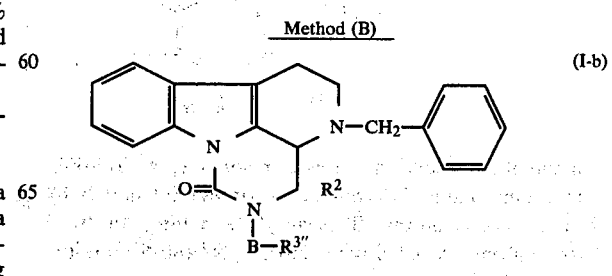

-continued

Method (B)

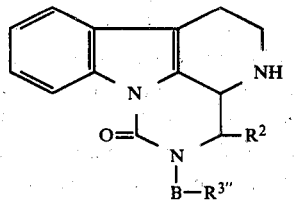
(I-b')

(In the above-mentioned reaction scheme, $R^{3''}$ is hydrogen, (lower alkoxy)carbonyl, lower alkoxy or (tetrahydropyran-2-yl)oxy, and $R^2$ and B are the same as defined above.)

Method (C)

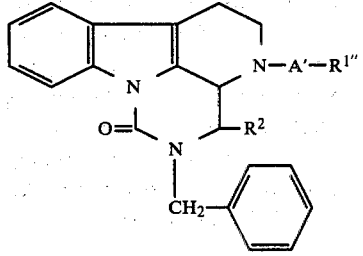
(I-c)

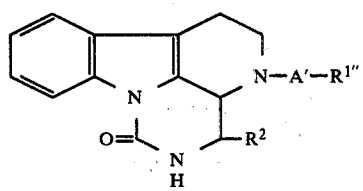
(I-c')

(In the above-mentioned reaction scheme, $R^{1''}$ is hydrogen or cycloalkyl having 3 to 6 carbon atoms, and $R^2$ and A' are the same as defined above.)

Method (D)

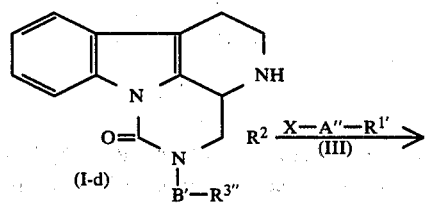
(I-d) $\xrightarrow{X-A''-R^{1'}}_{(III)}$

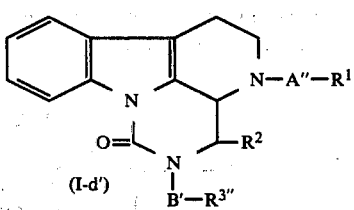
(I-d')

(In the above-mentioned reaction scheme, A" is alkylene having one to 5 carbon atoms or alkenylene having 2 to 5 carbon atoms, B' is alkylene having one to 5 carbon atoms, X is halogen, and $R^{1'}$, $R^2$ and $R^{3''}$ are the same as defined above.)

Method (E)

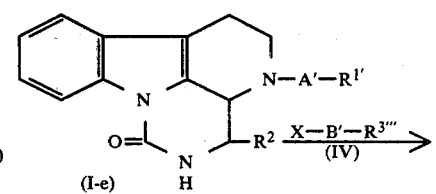
(I-e) $\xrightarrow{X-B'-R^{3'''}}_{(IV)}$

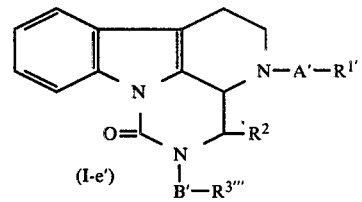
(I-e')

(In the above-mentioned reaction scheme, $R^{3'''}$ is hydrogen, phenyl, (lower alkoxy)carbonyl, lower alkoxy, di(lower alkyl)amino or (tetrahydropyran-2-yl)oxy, and $R^{1'}$, $R^2$, A', B' and X are the same as defined above.)

Method (F)

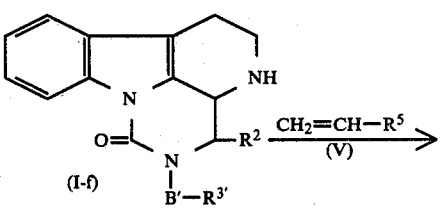
(I-f) $\xrightarrow{CH_2=CH-R^5}_{(V)}$

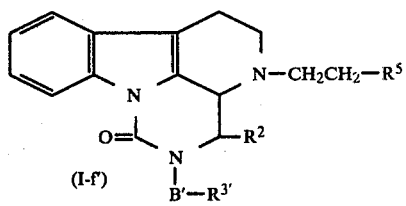
(I-f')

(In the above-mentioned reaction scheme, $R^5$ is (lower alkoxy)carbonyl, or (lower alkyl) carbonyl, and $R^2$, $R^{3'}$ and B' are the same as defined above.)

Method (G)

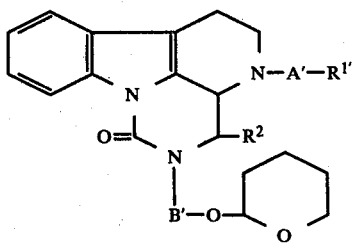
(I-g)

-continued

Method (G)

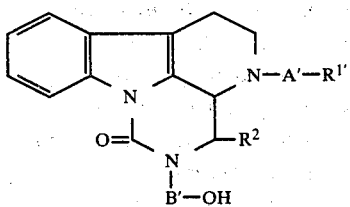
(I-g')

(In the above-mentioned reaction scheme, R¹', R², A' and B' are the same as defined above.)

Method (H)

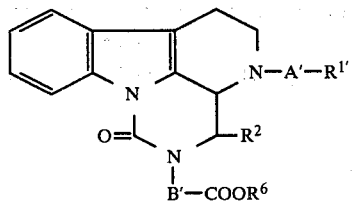
(I-h)

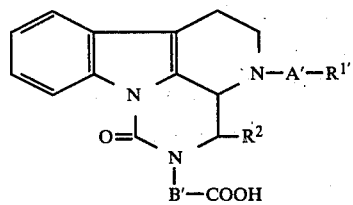
(I-h')

(In the above-mentioned reaction scheme, $R^6$ is lower alkyl, and R¹', R², A' and B' are the same as defined above.)

Method (I)

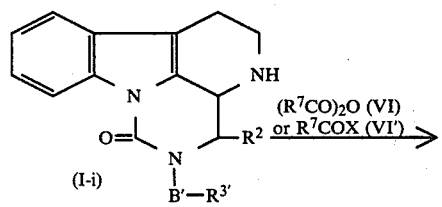
(I-i)

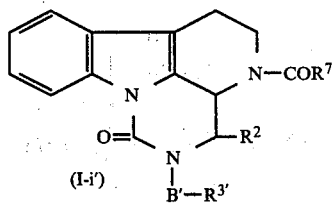
(I-i')

(In the above-mentioned reaction scheme, $R^7$ is lower alkyl, and R², R³', B' and X are the same as defined above.)

The method (A) comprises intramolecular cyclization of a 1,2,3,4-tetrahydro-β-carboline compound (II) to give a 1-oxo-1H-2,3,3a,4,5,6-hexahydro-2,4,10b-triazafluoranthene compound (I-a). The intramolecular cyclization may be carried out in an inert solvent in the presence of an alkali metal hydride (e.g., sodium hydride, potassium hydride), an alkali metal amide (e.g., sodium amide, potassium amide), an alkali metal alkoxide (e.g., sodium methoxide, potassium methoxide, sodium ethoxide, potassium ethoxide, sodium amyloxide, potassium amyloxide), lithium diisopropylamine, hexamethyldisilazane sodium salt (i.e., $((CH_3)_3Si)_2N.Na$) or triphenylphosphine sodium salt. Examples of the solvent include benzene, toluene, xylene, mesitylene, ether, tetrahydrofuran, dioxane and the like. It is preferred to carry out the reaction at a temperature between −15° and 170° C., especially at a temperature between 50° and 150° C. Alternatively, the intramolecular cyclization may be carried out in an inert solvent in the presence of 1,8-diazabicyclo(5,4,0)undecene-7 or 1,5-diazabicyclo(4,3,0)-nonene-5. Examples of the solvent include benzene, toluene, xylene, ether, tetrahydrofuran, dioxane and the like. It is preferred to carry out the reaction at a temperature between 50° and 150° C.

The method (B) comprises debenzylating a 1-oxo-4-benzyl-1H-2,3,3a,4,5,6-hexahydro-2,4,10b-triazafluoranthene compound (I-b) to give a 1-oxo-4-unsubstituted-1H-2,3,3a,4,5,6-hexahydro-2,4,10b-triazafluoranthene compound (I-b'). The debenzylation of the compound (I-b) may be accomplished by subjecting said compound to catalytic hydrogenation. Said catalytic hydrogenation may be carried out in the presence of a catalyst under a hydrogen atmosphere. It is preferred to carry out the reaction in the presence of an acid (e.g., hydrochloric acid, hydrobromic acid, acetic acid). It is also preferred to carry it out at a temperature of 20° to 60° C. Examples of the catalyst include palladium-carbon, palladium-black, palladium-silk, colloidal palladium, platinum oxide, rhodium, rhodium-alumina and the like. An alkanol (e.g., methanol, ethanol, propanol) or a mixture of said alkanol and water are suitable as the reaction solvent.

The method (C) comprises debenzylating a 1-oxo-2-benzyl-1H-2,3,3a,4,5,6-hexahydro-2,4,10b-triazafluoranthene compound (I-c) to give a 1-oxo-2-unsubstituted-1H-2,3,3a,4,5,6-hexahydro-2,4,10b-triazafluoranthene compound (I-c'). The debenzylation of the compound (I-c) may be accomplished by subjecting said compound to catalytic hydrogenation. Said catalytic hydrogenation of the compound (I-c) is carried out in the same manner as described in the aforementioned method (B). Alternatively, the debenzylation of the compound (I-c) may be carried out by treating said compound in liquid ammonia in the presence of an alkali metal. Examples of the alkali metal include sodium and potassium. It is preferred to carry out the reaction at a temperature between −50° and 30° C.

The method (D) comprises reacting a 1-oxo-4-unsubstituted-1H-2,3,3a,4,5,6-hexahydro-2,4,10b-triazafluoranthene compound (I-d) with a halide compound (III) to give a 1-oxo-4-substituted-1H-2,3,3a,4,5,6-hexahydro-2,4,10b-triazafluoranthene compound (I-d'). The reaction of the compound (I-d) with the compound (III) may be carried out in the presence of an acid acceptor in an inert solvent. Examples of said acid acceptor include an alkali metal carbonate (e.g., sodium carbonate, potassium carbonate), an alkali metal hydride (e.g., sodium hydride, potassium hydride), an alkali metal amide (e.g., sodium amide, potassium amide), an alkali metal alkoxide (e.g., sodium methoxide, potassium methoxide, sodium ethoxide, potassium ethoxide, sodium amyloxide, potassium amyloxide), lithium diisopropylamine, hexamethyldisilazane sodium salt, triphenylphosphine sodium salt and the like. Examples of the solvent include acetonitrile, dimethylformamide, dimethylsulfoxide, an alkanol (e.g., methanol, ethanol, propanol), chloroform, benzene, toluene, xylene and the like. It is preferred to carry out the reaction at a temperature between −15° and 150° C., especially at a temperature between 20° and 100° C.

The method (E) comprises reacting a 1-oxo-2-unsubstituted-1H-2,3,3a,4,5,6-hexahydro-2,4,10b-triazafluoranthene compound (I-e) with a halide compound (IV) to give a 1-oxo-2-substituted-1H-2,3,3a,4,5,6-hexahydro-2,4,10b-triazafluoranthene compound (I-e'). The reaction of the compound (I-e) with the copound (IV) may be carried out in the same manner as described in the aforementioned method (D).

The method (F) comprises reacting a 1-oxo-4-unsubstituted-1H-2,3,3a,4,5,6-hexahydro-2,4,10b-triazafluoranthene compound (I-f) with a vinyl compound (V) to give a 1-oxo-4-substituted-1H-2,3,3a,4,5,6-hexahydro-2,4,10b-triazafluoranthene compound (I-f'). The reaction of the compound (I-f) with the compound (V) may be carried out by stirring a mixture of said compounds at a temperature between −15° and 150° C. It is preferred to carry out the reaction in the presence of an acid (e.g., formic acid, acetic acid, trifluoroacetic acid, borontrifluoride-etherate, p-toluenesulfonic acid, methanesulfonic acid, sulfuric acid, hydrochloric acid, hydrobromic acid).

The method (G) comprises hydrolyzing a 1-oxo-2-((tetrahydropyran-2-yl-oxy)alkyl)-1H-2,3,3a,4,5,6-hexahydro-2,4,10b-triazafluoranthene compound (I-g) to give a 1-oxo-2-hydroxyalkyl-1H-2,3,3a,4,5,6-hexahydro-2,4,10b-triazafluoranthene compound (I-g'). The hydrolysis of the compound (I-g) may be carried out by treating said compound with an acid in an inert solvent. Examples of said acid include hydrochloric acid, hydrobromic acid, sulfuric acid and the like. A mixture of water and an alkanol (e.g., methanol, ethanol, propanol) is suitable as the solvent. It is preferred to carry out the reaction at a temperature between 0° and 100° C.

The method (H) comprises hydrolyzing a 1-oxo-2-alkoxycarbonylalkyl-1H-2,3,3a,4,5,6-hexahydro-2,4,10b-triazafluoranthene compound (I-h) to give a 1-oxo-2-carboxyalkyl-1H-2,3,3a,4,5,6-hexahydro-2,4,10b-triazafluoranthene compound (I-h'). The hydrolysis of the compound (I-h) may be carried out by treating said compound with an alkali in an inert solvent. Examples of said alkali include an alkali metal hydroxide (e.g., sodium hydroxide, potassium hydroxide), an alkali metal carbonate (e.g., sodium carbonate, potassium carbonate, sodium bicarbonate) and the like. A mixture of water and an alkanol (e.g., methanol, ethanol, propanol) is suitable as the solvent. It is preferred to carry out the reaction at a temperature between 0° C. and 100° C.

The method (I) comprises reacting a 1-oxo-4-unsubstituted-1H,2,3,3a,4,5,6-hexahydro-2,4,10b-triazafluoranthene compound (I-i) with an aliphatic acid anhydride (VI) or an aliphatic acid halide (VI') to give a 1-oxo-4-alkanoyl-1H- 2,3,3a,4,5,6-hexahydro-2,4,10b-triazafluoranthene compound (I-i'). The reaction of the compound (I-i) with the compound (VI) may be carried out by stirring a mixture of said compounds in an inert solvent. Examples of the solvent include pyridine, dimethylformamide, chloroform, ethyl acetate, acetonitrile, dichloromethane, benzene, toluene, dimethylsulfoxide and acetone. It is preferred to carry out the reaction at a temperature between −15° and 100° C. On the other hand, the reaction of the compound (I-i) with the compound (VI') may be carried out in the presence of an acid acceptor in an inert solvent. Examples of said acid acceptor include an alkali metal hydroxide (e.g., sodium hydroxide, potassium hydroxide), an alkali metal carbonate (e.g., sodium carbonate, potassium carbonate, sodium bicarbonate, potassium bicarbonate), an organic base (e.g., pyridine, collidine, triethylamine, N,N'-dimethylaniline) and the like. Examples of the solvent are an organic solvent (e.g., pyridine, dimethylformamide, chloroform, ethyl acetate, acetonitrile, dichloromethane, benzene, toluene, dimethylsulfoxide, acetone) and a mixture of said organic solvent and water. It is preferred to carry out the reaction at a temperature between −15° and 100° C.

The starting compound of the present invention, i.e., the compound (II), may be prepared by any one of the methods (J) through (L) described in the following reaction schemes.

Method (J)

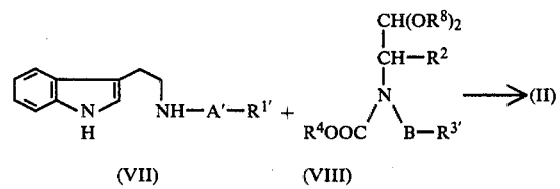

Method (K)

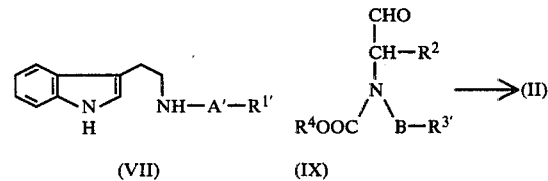

Method (L)

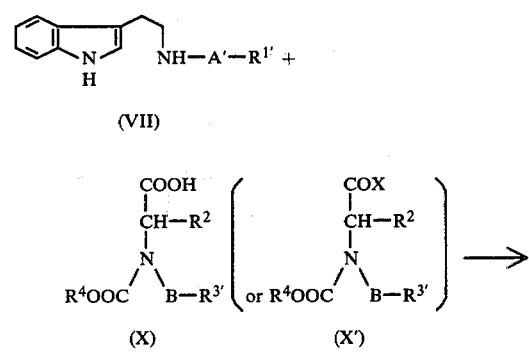

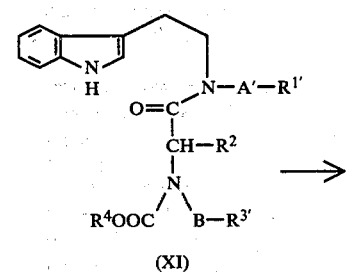

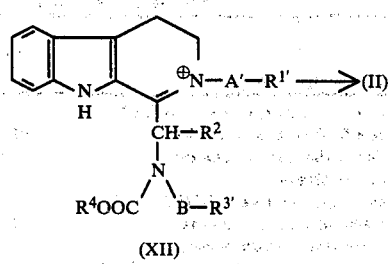

(XII)

(In the above-mentioned reaction schemes, $R^8$ is lower alkyl, and $R^{1'}$, $R^2$, $R^{3'}$, A', B and X are the same as defined above).

The method (J), i.e., the reaction of a N-substituted tryptamine (VII) with an aminoacetal derivative (VIII), may be carried out at a temperature between 20° and 150° C. in the presence or absence of an acid (e.g., hydrochloric acid, sulfuric acid, p-toluenesulfonic acid, acetic acid), thionyl chloride or boron trifluoride in an inert solvent (e.g., methanol, ethanol, propanol, acetonitrile, benzene, toluene, xylene, chloroform, dichloromethane, ether, tetrahydrofuran, dioxane, dimethylforamide, water). Alternatively, the reaction may be carried out at a temperature between −10° and 50° C. under mild alkaline conditions (e.g., pH 7–10) in such an inert solvent as mentioned above. An alkali metal hydroxide (e.g., sodium hydroxide, potassium hydroxide) or an alkali metal carbonate (e.g., sodium carbonate, potassium carbonate, sodium bicarbonate) are preferably employed to adjust the pH of the solution. Concomitantly, the compound (VIII) may be prepared by reacting an aminoacetaldehyde dialkylacetal or a N-alkyl (or N-benzyl) derivative thereof (said derivative being prepared by reacting a haloacetaldehyde dialkylacetal with an alkyl (or benzyl) amine) with an alkoxycarbonyl (or benzyloxycarbonyl) halide.

The method (K), i.e., the reaction of a N-substituted tryptamine compound (VII) with an aminoacetaldehyde derivative (IX), may be carried out in the same manner as described in the aforementioned method (J). The compound (IX) may be prepared in accordance with the method described in Chem. Pharm. Bull (Tokyo), 23(12), 3081–3087 (1975); J. Antibiotics, 29(No. 9), 600–601(1976); or J. Org. Chemistry, 43(No. 4), 754–755(1978).

The method (L) comprises the steps of reacting a N-substituted tryptamine compound (VII) with an amino acid derivative (X) or (X') to give a N,N-di-substituted tryptamine compound (XI), subjecting the compound (XI) to intramolecular cyclization to give a 3,4-dihydro-β-carbolinium compound (XII), and then reducing the compound (XII). The reaction of the compound (VII) with the compound (X) may be carried out at a temperature between −50° and 30° C. in the presence of an alkyl chloroformate (e.g., isobutyl chloroformate), benzyl chloroformate, a substituted benzyl chloroformate (e.g., p-methylbenzyl chloroformate) or pivaloyl chloride in an inert solvent (e.g., benzene, toluene, ethyl acetate, acetonitrile, ether, tetrahydrofuran, dioxane, chloroform, acetone, dimethylformamide). Alternatively, the reaction of the compound (VII) with the compound (X) may be carried out at a temperature between −50° and 30° C. in the presence of a dehydrating agent (e.g., dicyclohexylcarbodiimde) and p-nitrophenol, trichlorophenol, N-hydroxysuccinimide or N-hydroxyphthalimide in such an inert solvent as mentioned above. The reaction of the compound (VII) with the compound (X') may be carried out at a temperature between −15° and 50° C. in the presence of an acid acceptor (e.g., pyridine, triethylamine, dimethylaniline, sodium hydroxide, potassium hydroxide, sodium carbonate, potassium carbonate, sodium bicarbonate) in an inert solvent (e.g., benzene, ethyl acetate, acetonitrile, ether, tetrahydrofuran, dioxane, dichloromethane, chloroform, diemthylformamide). The intramolecular cyclization of the compound (XI) may be carried out at a temperature between 20° and 150° C. in the presence of phosphorus oxychloride, phosphorus oxybromide, phosphorus pentachloride, polyphosphoric acid, ethyl polyphosphate in an inert solvent (e.g., acetonitrile, benzene, toluene, xylene, chloroform, pyridine). When phosphorus oxychloride or phosphorus oxybromide is used, however, it is not always necessary to use the solvent because said agent serves as the solvent. The subsequent reduction of the compound (XII) may be carried out by treating it with a reducing agent (e.g., sodium borohydride, potassium borohydride, lithium borohydride, diborane) at a temperature between −15° and 50° C. in an inert solvent (e.g., water, aqueous tetrahydrofuran, aqueous dioxane, acetonitrile, methanol, ethanol, propanol, ethyl acetate). Alternatively, said reduction may be carried out by catalytic hydrogenation at a temperature between 20° and 150° C. in the presence of a catalyst (e.g., Raney nickel, palladium-carbon, palladium-black, palladium-silk, colloidal palladium, platinum oxide, rhodium-alumina) in an inert solvent (e.g., methanol, ethanol, propanol, water).

In view of the potent anti-anoxic activity of the triazafluoranthene compound (I) obtained hereinbefore, said compound of the present invention is useful for treatment or prophylaxis of various hypoxia which may occur due to cerebral apoplexia, craniotrauma or brain ischemia. For example, it may be employed for treatment or prophylaxis of amnesia, disorientation, clouding of consciousness and other conscious disturbances. The compound (I) of the invention may also be employed for treatment of patients who are undergoing long-lasting surgical procedures involving the liability of transitory cerebral hypoxia.

Moreover, the compound (I) of the present invention has a potent preventive effect upon lipid peroxides formation in living bodies. For example, when the preventive effect of a test compound upon lipid peroxides formation was estimated by using rat brain homogenate or mitochondria (cf. Bioch. Pharmacol. Vol. 25, pages 2233 –2236(1976) and Brain Research, Vol. 158, pages 423 –434(1978), said effect of 1-oxo-2-methyl-4-pentyl-1H-2,3,3a,4,5,6-hexahydro-2,4,10b-triazafluoranthene hydrochloride and 1-oxo-2-ethyl-4-n-pentyl-1H,2,3,3a,4,5,6-hexahydro-2,4,10b-triazafluoranthene methanesulfonate were 6 to 10 times stronger than that of α-tocopherol. Lipid peroxides levels in tissues of mammalian species are known to increase with age and cause cell death and/or damage with a consequent change of cell permeability. In addition, lipid peroxides have been suggested to be a primary etiologic factor in the genesis of stroke (cf. Stroke, Vol. 10, No. 3, pages 323–326(1979)). Thus, the compound (I) may be used to improve the lipid peroxides levels in the tissues of the aged subjects.

The compound (I) of the present invention can be used for pharmaceutical use as either the free base or a pharmaceutically acceptable acid addition salt thereof.

Examples of the acid addition salts include inorganic acid addition salts such as hydrochloride, hydrobromide, nitrate, sulfate and phosphate; and organic acid addition salts such as formate, acetate, oxalate, fumarate, maleate, citrate, lactate, nicotinate, benzoate and methanesulfonate. The compound (I) of the present invention may be administered either orally or parenterally, and may be further used in conjunction or admixture with a pharmaceutical excipient which is suitable for oral or parenteral administration. The excipient selected must be one which does not react with the compound (I). Suitable excipients include, for example, gelatin, lactose, glucose, sodium chloride, starch, magnesium stearate, talcum, vegetable oil and so forth. Other known medicinal excipients may be employed. The pharmaceutical preparation may be a solid dosage form such as a tablet, a coated tablet, a pill or a capsule, or a liquid dosage form such as a solution, a suspension or an emulsion. The pharmaceutical preparation may be sterilized and/or contain auxiliaries such as preserving and stabilizing agents. The dose of the compound (I) for pharmaceutical use may vary dependent on the route of administration; the age, weight and condition of patients; and particular disease to be treated. In general, it may be used for pharmaceutical use at a dose of one to 100 mg/kg, especially 3 to 30 mg/kg, per day.

Practical and presently-preferred embodiments of the present invention are illustratively shown in the following Examples. Throughout the specification and claims, the terms "lower alkyl" and "lower alkoxy" should be interpreted as referring to alkyl or alkoxy having one to 4 carbon atoms.

Experiment I (Anti-anoxic activity)

A suspension of a test compound in 0.5% carboxymethylcellulose was administered intraperitoneally to a group of male mice weighing about 20 g. Fifteen minutes after administration of the test compound, the mice were placed in an atmosphere impoverished in oxygen by creating a partial vacuum (165 mmHg). Then, the survival time of each mice was measured with a chronometer.

The results are shown in the following Table 1.

TABLE 1

| Test compounds | Dose (mg/kg) | Survival time (seconds) mean ± S.E. |
|---|---|---|
| 1-oxo-1H-2,3,3a,4,5,6-hexahydro-2,4,10b-triazafluoranthene hydrochloride | 10 | 98.3 ± 12.08 |
| | 30 | 195.5 ± 23.46 |
| 1-oxo-2-methyl-1H-2,3,3a,4,5,6-hexahydro-2,4,10b-triazafluoranthene hydrochloride | 10 | 79.2 ± 3.31 |
| | 30 | 121.1 ± 14.50 |
| | 60 | 134.1 ± 14.56 |
| 1-oxo-2-ethyl-4-methyl-1H-2,3,3a,4,5,6-hexahydro-2,4,10b-triazafluoranthene hydrochloride | 60 | 146.3 ± 20.2 |
| | 100 | 160.9 ± 14.00 |
| 1-oxo-4-ethyl-1H-2,3,3a,4,5,6-hexahydro-2,4,10b-triazafluoranthene hydrochloride | 10 | 91.2 ± 4.91 |
| | 20 | 114.1 ± 8.33 |
| | 30 | 139.3 ± 19.06 |
| 1-oxo-2-benzyl-4-ethyl-1H-2,3,3a,4,5,6-hexahydro-2,4,10b-triazafluoranthene hydrochloride | 30 | 109.4 ± 14.48 |
| | 60 | 121.8 ± 19.90 |
| | 100 | 157.8 ± 21.02 |
| 1-oxo-2-methyl-4-n-propyl-1H-2,3,3a,4,5,6-hexahydro-2,4,10b-triazafluoranthene hydrochloride | 30 | 86.1 ± 2.83 |
| | 60 | 140.5 ± 12.5 |
| | 100 | 173.6 ± 10.98 |
| 1-oxo-2-methyl-4-isopropyl-1H-2,3,3a,4,5,6-hexahydro-2,4,10b-triazafluoranthene hydrochloride | 30 | 92.3 ± 5.01 |
| | 60 | 163.7 ± 13.20 |
| | 100 | 188.2 ± 9.10 |
| 1-oxo-2-methyl-4-n-butyl-1H-2,3,3a,4,5,6-hexahydro-2,4,10b-triazafluoranthene hydrochloride | 30 | 74.9 ± 1.56 |
| | 60 | 103.5 ± 7.73 |
| | 100 | 195.9 ± 18.89 |

TABLE 1-continued

| Test compounds | Dose (mg/kg) | Survival time (seconds) mean ± S.E. |
|---|---|---|
| 1-oxo-2,3-dimethyl-4-n-butyl-1H-2,3,3a,4,5,6-hexahydro-2,4,10b-triazafluoranthene (trans isomer) hydrochloride | 100 | 134.8 ± 6.94 |
| 1-oxo-2-ethyl-4-n-butyl-1H-2,3,3a,4,5,6-hexahydro-2,4,10b-triazafluoranthene hydrochloride | 100 | 145.4 ± 12.2 |
| 1-oxo-2-isopropyl-4-n-butyl-1H-2,3,3a,4,5,6-hexahydro-2,4,10b-triazafluoranthene hydrochloride | 100 | 149.8 ± 11.27 |
| 1-oxo-2-(2-ethoxyethyl)-4-n-butyl-1H-2,3,3a,4,5,6-hexahydro-2,4,10b-triazafluoranthene hydrochloride | 100 | 141.8 ± 10.5 |
| 1-oxo-2-methyl-4-n-pentyl-1H-2,3,3a,4,5,6-hexahydro-2,4,10b-triazafluoranthene hydrochloride | 30 | 68.8 ± 1.87 |
| | 100 | 114.6 ± 14.9 |
| | 300 | 175.0 ± 11.29 |
| 1-oxo-2-ethyl-4-n-pentyl-1H-2,3,3a,4,5,6-hexahydro-2,4,10b-triazafluoranthene methanesulfonate | 100 | 145.1 ± 13.5 |
| 1-oxo-2-methyl-4-cyclohexylmethyl-1H-2,3,3a,4,5,6-hexahydro-2,4,10b-triazafluoranthene hydrochloride | 30 | 89.1 ± 4.63 |
| | 100 | 131.6 ± 15.25 |
| 1-oxo-2,3-dimethyl-4-benzyl-1H-2,3,3a,4,5,6-hexahydro-2,4,10b-triazafluoranthene(trans isomer) hydrochloride | 30 | 69.5 ± 5.54 |
| | 60 | 81.1 ± 5.75 |
| | 100 | 176.5 ± 20.16 |
| 1-oxo-2-methyl-4-phenethyl-1H-2,3,3a,4,5,6-hexahydro-2,4,10b-triazafluoranthene methanesulfonate | 30 | 65.5 ± 3.51 |
| | 100 | 96.2 ± 4.91 |
| Control* | | 61.7 ± 0.47 |

Note:
*a group of mice (70 mice) to which no test compound was administered.

Experiment II (Anti-anoxic acitivity)

A suspension of a test compound in 0.5% carboxymethylcellulose was administered intraperitoneally to a group of male mice weighing about 20 g. Fifteen minutes after administration of the test compound, the lethal dose (3 mg/kg) of potassium cyanide was administered intravenously to said mice. Then, $PTD_{50}$ (i.e., the dose required to produce 50% increase in the survival time of mice as compared with that of a group of non-medicated mice) of the test compound was calculated from the dose-response curve obtained. Simultaneously, $PD_{50}$ (i.e., the dose required to protect 50% of the mice from KCN-induced death) of the test compound was calculated from the number of mice died during the experiments.

The results are shown in the following Table 2.

TABLE 2

| | Anti-anoxic activity | |
|---|---|---|
| Test compounds | $PTD_{50}$ (mg/kg) | $PD_{50}$ (mg/kg) |
| 1-oxo-2-methyl-4-ethyl-1H-2,3,3a,4,5,6-hexahydro-2,4,10b-triazafluoranthene hydrochloride | 7.8 | 43.2 |
| 1-oxo-2-methyl-4-n-butyl-1H-2,3,3a,4,5,6-hexahydro-2,4,10b-triazafluoranthene hydrochloride | 24.0 | 49.5 |
| 1-oxo-2-methyl-4-n-propyl-1H-2,3,3a,4,5,6-hexahydro-2,4,10b-triazafluoranthene hydrochloride | 21.6 | 53.8 |
| 1-oxo-2-methyl-4-n-pentyl-1H-2,3,3a,4,5,6-hexahydro-2,4,10b-triazafluoranthene hydrochloride | 13.4 | 51.8 |

Experiment III (Preventive effect on lipid peroxide formation)

0.1 ml of an ethanol or physiological saline solution containing $10^{-5}$ M of a test compound was added to a mixture of 2.4 ml of 0.067 M potassium phosphate buffer solution (pH 7.4) and 0.5 ml of 10% rat brain-homogenate. After a 30-minute incubation of the mixture at 37° C., one ml of 20% trichloroacetic acid was added thereto, and lipid peroxide formations were determined by the thiobarbituric acid colorimetric method (J. Robak et al., Biochem. Pharmacol., Vol. 25, page 2233 (1976)). Suppression (%) of lipid peroxide formation of the test compound was calculated according to the following formula:

$$\text{Suppression (\%) of lipid peroxide formation} = \left[1 - \frac{\Delta OD \text{ of test group*}}{\Delta OD \text{ of control group**}}\right] \times 100$$

Note:
*group containing the test compound
**group containing an equal volume of ethanol or a physiological saline solution instead of the test compound solution.
$\Delta OD$ was calculated as [(optical density measured at 532 nm) − (optical density measured at 600 nm)]

The results are shown in the following Table 3.

TABLE 3

| Test compounds | Suppression (%) of lipid peroxide formation |
| --- | --- |
| 1-oxo-2-methyl-4-n-butyl-1H-2,3,3a,4,5,6-hexahydro-2,4,10b-triazafluoranthene hydrochloride | 51.2 |
| 1-oxo-2,3-dimethyl-4-n-butyl-1H-2,3,3a,4,5,6-hexahydro-2,4,10b-triazafluoranthene (trans isomer) hydrochloride | 73.4 |
| 1-oxo-2-ethyl-4-n-butyl-1H-2,3,3q,4,5,6-hexahydro-2,4,10b-triazafluoranthene hydrochloride | 50.4 |
| 1-oxo-2-isopropyl-4-n-butyl-1H-2,3,3a,4,5,6-hexahydro-2,4,10b-triazafluoranthene hydrochloride | 58.3 |
| 1-oxo-2-(2-ethoxyethyl)-4-n-butyl-1H-2,3,3a,4,5,6-hexahydro-2,4,10b-triazafluoranthene hydrochloride | 52.2 |
| 1-oxo-2-methy-4-isobutyl-1H-2,3,3a,4,5,6-hexahydro-2,4,10b-triazafluoranthene hydrochloride | 59.9 |
| 1-oxo-2-methyl-4-n-pentyl-1H-2,3,3a,4,5,6-hexahydro-2,4,10b-triazafluoranthene hydrochloride | 60.2 |
| 1-oxo-2-ethyl-4-n-pentyl-1H-2,3,3a,4,5,6-hexahydro-2,4,10b-triazafluoranthene methanesulfonate | 62.8 |
| 1-oxo-2-methyl-4-cyclohexylmethyl-1H-2,3,3a,4,5,6-hexahydro-2,4,10b-triazafluoranthene hydrochloride | 64.7 |
| 1-oxo-2,3-dimethyl-4-benzyl-1H-2,3,3a,4,5,6-hexahydro-2,4,10b-triazafluoranthene (trans isomer) hydrochloride | 67.3 |
| 1-oxo-2-methyl-4-phenethyl-1H-2,3,3a,4,5,6-hexahydro-2,4,10b-triazafluoranthene methanesulfonate | 53.6 |
| (Control) α-Tocophelol | 11.6 |

EXAMPLE 1

To a solution of 50 g of N-benzyl-tryptamine hydrochloride (i.e., 3-(2-(benzylamino)-ethyl)indole hydrochloride) in 500 ml of methanol-water (4:1) are added 57.9 g of N-benzyloxycarbonyl-aminoacetaldehyde diethylacetal and 25 ml of 10% hydrochloric acid, and the mixture is refluxed for 16 hours. After the reaction, the reaction mixture is evaporated under reduced pressure to remove solvent, and the resultant crystals are collected by filtration. After being washed with water and ether, said crystals are added to a saturated sodium bicarbonate solution, and then extracted with ethyl acetate. The extract is washed with water, dried and then evaporated to remove solvent. The residue (oil, 60 g) is purified by silica gel chromatography (Solvent: chloroform-methanol (20:1)). 46 g of 1,2,3,4-tetrahydro-1-((N-benzyloxycarbonylamino)methyl)-2-benzyl-β-carboline are thereby obtained as a caramel. Yield: 62%

IR$\nu_{max}^{nujol}$ (cm$^{-1}$): 3400, 3300, 1700.

NMR (δ, CDCl$_3$): 8.25 (broad s, 1H, >NH), 5.40 (broad s, 1H, —NHCOOCH$_2$C$_6$H$_5$), 5.03 (s, 2H, —COOC$\underline{H}_2$C$_6$H$_5$), 3.74 (s, 2H, >N—C$\underline{H}_2$C$_6$H$_5$).

Mass (m/e): 425 (M$^+$).

Hydrochloride:

M.p. 186.5°–188° C. (decomp.) (colorless prisms) (recrystallized from methanol).

IR$\nu_{max}^{nujol}$ (cm$^{-1}$): 3540, 3200, 2700 - 1710, 1615.

Methanesulfonate:

M.p. 191°–192° C. (colorless fine needles) (recrystallized from ethanol).

IR$\nu_{max}^{nujol}$ (cm$^{-1}$): 3250, 3160, 1710, 1540.

EXAMPLE 2

A solution of 4.0 g of N-benzyloxcarbonyl-aminoacetaldehyde diethylacetal in 15 ml of ethanol, 30 ml of acetic acid and 0.9 ml of conc. hydrochloric acid are added to 1.88 g of N-ethyl-tryptamine (i.e., 3-(2-(ethylamino)ethyl)indole), and the mixture is refluxed for 24 hours. After the reaction, the reaction mixture is condensed, and the residue is alkalized with a saturated sodium bicarbonate solution under cooling and then extracted with ethyl acetate. The extract is washed with water, dried and then evaporated to remove solvent. The residue (yellow oil, 4.60 g) thus obtained is purified by silica gel chromatography (Solvent: chloroform-methanol (30:1)). 2.76 g of 1,2,3,4-tetrahydro-1-((N-benzyloxycarbonylamino)methyl)-2-ethyl-β-carboline are thereby obtained.

Yield: 76%.

M.P. 92°–94° C. (colorless prisms) (recrystallized from n-hexane).

IR$\nu_{max}^{nujol}$ (cm$^1$): 3375, 3330, 1705, 1520.

NMR (δ, CDCl$_3$): 8.50 (s,1H, >N$\underline{H}$), 7.39 (s, 5H, —COOCH$_2$C$_6\underline{H}_5$), 5.66 (s, 1H, —CH$_2$N$\underline{H}$-COOCH$_2$C$_6$H$_5$), 5.17 (s, 2H, —COO—C$\underline{H}_2$C$_6$H$_5$), 1.10 (t, 3H, J=7 Hz, >N—CH$_2$C$\underline{H}_3$).

Mass (m/e): 379 (M$^+$).

EXAMPLE 3

To a solution of 5.0 g of N-n-butyl-tryptamine (i.e., 3-(2-(n-butylamino)ethyl)-indole) in 45 ml of methanol-water (2:1) are added 5.93 g of N-ethoxycarbonylaminoacetaldehyde diethylacetal and 3 ml of 10% hydrochloric acid, and the mixture is refluxed for 18 hours. After the reaction, the reaction mixture is condensed under reduced pressure, and the residue is alkalized with a saturated sodium bicarbonate solution and then extracted with ethyl acetate. The extract is washed with water, dried and then evaporated to remove solvent. The residue (8.2 g) thus obtained is purified by silica gel chromatography (Solvent: Chloroform-methanol (50:1)). 2.26 g of 1,2,3,4-tetrahydro-1-(N-ethoxycarbonylamino)methyl)-2-n-butyl-β-carboline are thereby obtained as an oil. Yield: 29.8%

IR$\nu_{max}^{film}$ (cm$^{-1}$): 3400, 3330, 1720 (sh), 1700, 1620.

NMR (δ, CDCl₃): 8.55 (broad s, 1H, >N$\underline{H}$), 7.52 - 6.90 (m, 4H, aromatic), 5.40 (broad s, 1H, —N$\underline{H}$COO), 4.10 (q, 2H, J=7 Hz, —COOC$\underline{H}_2$CH₃), 1.20 (t, 3H, J=7 Hz, —COOCH₂C$\underline{H}_3$), 1.0 - 0.8 (m, 3H, >N—(CH₂)₃C$\underline{H}_3$)

Mass (m/e): 329 (M+).

EXAMPLE 4

To a solution of 5.0 g of N-benzyl-tryptamine hydrochloride (i.e., 3-(2-(benzylamino)ethyl)indole hydrochloride) in 60 ml of methanol-water (2:1) are added 3.6 g of 2-(ethoxycarbonylamino)-propanol, and the mixture is refluxed for 24 hours. After the reaction, the reaction mixture is condensed. Chloroform is added to the residue, and the mixture is extracted with dil.hydrochloric acid. The aqueous layer is alkalized and then extracted with ethyl acetate. The extract is washed, dried and then evaporated to removed solvent. The residue (5.1 g) thus obtained is purified by silica gel chromatography (Solvent: 1% methanol-chloroform). 1.96 g of 1,2,3,4-tetrahydro-1-(1-(ethoxycarbonylamino)ethyl)-2-benzyl-β-carboline are thereby obtained as a pale yellow oil. Yield: 30%

IR$\nu_{max}^{CHCl_3}$ (cm⁻¹): 3430, 1705.

NMR (δ, CDCl₃): 8.0 (m, 1H, >N$\underline{H}$), 5.15 (m, 1H, —N$\underline{H}$CO), 4.1 (q, 2H, —C$\underline{H}_2$CH₃), 1.25 (t, 3H, —CH₂C$\underline{H}_3$), 1.18, 1.15 (d, d, 3H, J=6 Hz, J=6 Hz, —NH—CH—C$\underline{H}_3$).

Mass (m/e): 377 (M+).

EXAMPLE 5

(1) 30 ml of anhydrous tetrahydrofuran and 1.05 g of triethylamine are added to 2.17 g of N-benzyloxycarbonyl-glycine, and 1.43 g of isobutyl chloroformate are added dropwise thereto at −15° C. under stirring. A solution of 1.96 g of N-ethyl-tryptamin (i.e., 3-(2-ethylamino)ethylindole) in 40 ml of anhydrous tetrahydrofuran is added dropwise to the mixture at the same temperature, and said mixture is stirred at 0° C. for one hour and further stirred at room temperature for 16 hours. After the reaction, the reaction mixture is evaporated to remove solvent. The residue (oil) is purified by silica gel chromatography (Solvent: ethyl acetate-chloroform (1:1). 4.0 g of N-ethyl-N-(N-benzyloxycarbonylglycyl)-tryptamine are thereby obtained as a colorless oil. Yield: 100%.

IR$\nu_{max}^{film}$ (cm⁻¹): 3400, 3300, 1721, 1717, 1640.

NMR (δ,CDCl₃): 8.45 (broad s, 1H, >N$\underline{H}$), 7.75 -6.90 (m, 10H, aromatic), 5.90 (broad s, 1H, —N$\underline{H}$CO), 5.24, 5.20 (s, s, 2H, —C$\underline{H}_2$C₆H₅), 1.11, 1.07 (t, t, 3H, >N—CH₂C$\underline{H}_3$).

Mass (m/e): 379 (M+).

Rf-value: 0.65 (ethyl acetate-chloroform (1:1), on silica plate).

(2) 20 g of ethyl polyphosphate are added to 2.0 g of N-ethyl-N-(N-benzyloxycarbonylglycyl)-tryptamine, and the mixture is stirred at 60° C. for 2.5 hours. Then, 30 ml of water are added to the mixture under ice-cooling, and said mixture is adjusted to pH 3-4 with an aqueous 30% sodium hydroxide solution. 50 ml of methanol are added to the mixture, and sodium borohydride is added thereto until said mixture become alkaline (pH 10). The mixture is stirred at room temperature overnight. After the reaction, the reaction mixture is condensed, and the residue is extracted with ethyl acetate. The extract is washed with water, dried and then evaporated to remove solvent. The residue (2.5 g) thus obtained is purified by silica gel chromatography (Solvent: chloroform-methanol (19:1)). 0.61 g of 1,2,3,4-tetrahydro-1-((N-benzyloxycarbonylamino)methyl)-2-ethyl-β-carboline are thereby obtained. The physico-chemical properties of this product are identical with those of the product obtained in Example 2.

EXAMPLE 6

(1) 30 ml of anhydrous tetrahydrofuran and 1.16 g of triethylamine are added to 1.69 g of N-ethoxycarbonylglycine, and 1.57 g of isobutyl chloroformate are added dropwise thereto at −20° to −25° C. under stirring. The mixture is stirred at the same temperature for 10 minutes, and a solution of 2.47 g of N-n-butyl-tryptamine (i.e., 3-(2-(n-butylamino)ethyl)indole) in 30 ml of anhydrous tetrahydrofuran is added to said mixture at the same temperature. Then, the mixture is stirred at room temperature for 20 hours. After the reaction, the reaction mixture is evaporated to remove solvent, and water is added to the residue. The aqueous mixture is extracted with chloroform, and the extract is dried and then condensed. The residue (oil, 4.0 g) thus obtained is purified by silica gel chromatography (Solvent: chloroform-ethyl acetate (1:1)) 3.5 g of N-n-butyl-N-(N-ethoxycarbonylglycyl)-tryptamine are thereby obtained as an oil. Yield: 87.9%.

IR$\nu_{max}^{film}$ (cm⁻¹): 3600 - 3200, 1730, 1660, 1630.

NMR (δ, CDCl₃): 8.25 (broad s, 1H,>N$\underline{H}$), 7.80 -6.9 (m, 4H, aromatic), 5.65 (broad s, 1H, —N$\underline{H}$CO), 4.10 (q, 2H, J=7, Hz, —COOC$\underline{H}_2$CH₃), 1.25 (t,3H, J=7 Hz, —COOCH₂C$\underline{H}_3$), 1.05 - 0.70, (m, 3H, >N—(CH₂)₃C$\underline{H}_3$).

Mass (m/e): 346 (M+).

(2) To a solution of 3.40 g of N-n-butyl-N-(N-ethoxycarbonylglycyl)-tryptamine in 40 ml of anhydrous toluene are added 10 ml of phosphorus oxychloride, and the mixture is stirred at 120° C. for 45 minutes. The mixture is condensed under reduced pressure, and 100 ml of ethanol are added to the residue. Then, sodium borohydride is added to the mixture until said mixture becomes alkaline, and the mixture is stirred at room temperature for 30 minutes. After the reaction, the reaction mixture is condensed, and water is added to the residue. The aqueous mixture is extracted with chloroform, and the extract is washed, dried and then evaporated to remove solvent. The residue (oil, 4.0 g) thus obtained is purified by silica gel chromatography (Solvent: chloroform-ethyl acetate (1:1)). 2.50 g of 1,2,3,4-tetrahydro-1-((N-ethoxycarbonylamino)methyl)-2-n-butyl-β-carboline are thereby obtained as a pale yellow oil. Yield: 77.6% The physico-chemical properties of this product are identical with those of the product obtained in Example 3.

EXAMPLE 7

(1) 3.17 g of triethylamine are added to a solution of 5.06 g of N-ethoxycarbonyl-DL-alanine in 90 ml of anhydrous tetrahydrofuran, and 3.79 g of isobutyl chloroformate are added dropwise thereto at a temperature below −20° C. After the mixture is stirred at the same temperature for five minutes, a solution of 7.86 g of N-benzyl-tryptamine (i.e., 3-(2-(benzylamino)ethyl)indole) in 160 ml of anhydrous tetrahydrofuran is added dropwise to said mixture at −20° to −15° C. The mixture is stirred at the same temperature for one hour and further stirred at room temperature for one hour. After the reaction, the reaction mixture is evaporated to remove solvent. Ethyl acetate is added to the residue, and the mixture is washed with water, dried and then evaporated to remove solvent. The residue (11.2 g) thus obtained is purified by silica gel chromatography (Solvent: 1% methanol-chloroform). 9.39 g of N-benzyl-N-(N-ethoxycarbonylalanyl)-tryptamine are thereby obtained as a pale yellow powder. Yield: 76%

IR$\nu_{max}^{CHCl_3}$ (cm$^{-1}$): 3425, 1710, 1635, 1500 1450.

NMR (δ, CDCl$_3$): 8.2 (m, 1H, >N$\underline{H}$), 4.90, 4.31 (AB type, 2H, J=15 Hz, J=15 Hz, >N—C$\underline{H}_2$C$_6$H$_5$), 4.5 (m, 1H, —COC$\underline{H}$(CH$_3$)—NHCO), 4.12 (q, 2H, J=7.0 Hz, —COOC$\underline{H}_2$CH$_3$), 1.28 (d, 3H, J=6.7 Hz, —COCH(C$\underline{H}_3$)NHCO), 1.23 (t, 3H, J=7.0 Hz, —COOCH$_2$C$\underline{H}_3$)

Mass (m/e): 393 (M+), 251, 143 (base peak), 91.

(2) To a solution of 9.26 g of N-benzyl-N-(N-ethoxycabonylalanyl)-tryptamine in 100 ml of acetonitrile are added 10 ml of phosphorus oxychloride, and the mixture is refluxed under nitrogen gas atmosphere for 2.5 hours. The mixture is condensed under reduced pressure to dryness. 200 ml of methanol-water (1:1) are added to the residue, and sodium borohydride is added to the mixture until said mixture becomes alkaline (pH 9). Then, 300 ml of water are added to the mixture, and the aqueous mixture is extracted with ethyl acetate. The extract is washed with water, dried and then evaporated to remove solvent. The residue (8.7 g) thus obtained is purified by silica gel chromatography (Solvent: 1% methanol-chloroform). 3.13 g of 1,2,3,4-tetrahydro-1-(1-(N-ethoxycarbonylamino)-ethyl)-2 benzyl-β-carboline are thereby obtained as a pale yellow oil. Yield: 35% The physico-chemical properties of this product are identical with those of the product obtained in Example 4.

EXAMPLE 8

(1) 25 ml of anhydrous tetrahydrofuran and 0.165 g of triethylamine are added to 0.98 g of N-methyl-N-ethoxycarbonyl-glycine, and 0.83 g of isobutyl chloroformate are added dropwise thereto at −20° to −25°0 C. After the mixture is stirred at the same temperature for 10 minutes, a solution of 1.31 g of N-n-butyl-tryptamine (i.e., 3-(2-(n-butylamino)ethyl)indole) in 20 ml of anhydrous tetrahydrofuran is added at the same temperature to the mixture, and said mixture is stirred at room temperature for 26 hours. After the reaction, the reaction mixture is condensed, and then water is added to the residue. The aqueous mixture is extracted with ethylacetate, and the extracts are washed with water, dried and then evaporated to remove solvent. The residue (2.33 g) thus obtained is purified by silica gel chromatography (Solvent: chloroform-methanol (20:1)). 1.28 g of N-n-butyl-N-(N-methyl-N-ethoxycabonylglycyl)-tryptamine are thereby obtained as a yellow oil. Yield: 58.7%

IR$\nu_{max}^{film}$ (cm$^{-1}$): 3300, 1720 (sh), 1700, 1690, 1645.

NMR (δ,CDCl$_3$): 8.70 - 8.30 (m, 1H, >N$\underline{H}$), 7.70 - 6.90 (m, 4H, aromatic) 3.00 (s, 3H, >N—C$\underline{H}_3$), 1.80 - 1.05 (m, 9H, >N—(C$\underline{H}_2$)$_3$CH$_3$, —COOCH$_2$C$\underline{H}_3$), 1.05 - 0.7 (m, 3H, >N—(CH$_2$)$_3$C$\underline{H}_3$).

Mass (m/e): 359 (M+).

(2) To a solution of 1.2 g of N-n-butyl-N-(N-methyl-N-ethoxycarbonylglycyl)-tryptamine in 20 ml of anhydrous toluene are added 5 ml of phosphorus oxychloride, and the mixture is stirred at 120° C. for 2 hours. Then, the mixture is evaporated under reduced pressure to remove solvent. 80 ml of ethanol are added to the residue, and sodium borohydride is added thereto under ice-cooling until the mixture becomes alkaline. After the mixture is stirred for 30 minutes, the reaction mixture is condensed, and then water is added to the residue. The aqueous mixture is extracted with chloroform, and the extracts are washed with water, dried and then evaporated to remove solvent. The residue (1.0 g) thus obtained is purified by silica gel chromatography (Solvent: chloroform-methanol (50:1)). 0.48 g of 1,2,3,4-tetrahydro-1-((N-methyl-N-ethoxycarbonyl-amino)methyl)-2-n-butyl-β-carboline are thereby obtained as a yellow oil. Yield: 42.1%.

IR$\nu_{max}^{film}$ (cm$^{-1}$): 3400, 3300, 1700 (sh), 1680.

NMR (δ, CDCl$_3$): 8.50 (broad s, 1H, N$\underline{H}$), 7.60-6.85 (m, 4H, aromatic), 4.15 (q, 2H, —COOC$\underline{H}_2$CH$_3$), 3.00 (s, 3H, >N—CH$_3$), 1.70-1.1 (m, 9H, N—(C$\underline{H}_2$)$_3$CH$_3$, —COOCH$_2$ C$\underline{H}_3$), 1.1-0.7 (m, 3H, >N—(CH$_2$)$_3$C$\underline{H}_3$).

Mass (m/e): 343 (M+).

EXAMPLE 9

10.0 g of 63% sodium hydride are suspended in 600 ml of anhydrous benzene, and a solution of 45 g of 1,2,3,4-tetrahydro-1-((N-benzyloxycarbonylamino)methyl)-2-benzyl-β-carboline in 300 ml of anhydrous benzene is added to the suspension under stirring. After the mixture is stirred for 30 minutes, said mixture is refluxed for one hour. After cooling, the crystalline precipitates are collected by filtration, washed with water and ether, and then recrystallized from methanol. 28 g of 1-oxo-4-benzyl-1H-2,3,3a,4,5,6-hexahydro-2,4,10b-triazafluoranthene are thereby obtained as colorless needles. Yield: 83%.

M.p. 226°–229° C. (decomp.).

IR$\nu_{max}^{nujol}$ (cm$^{-1}$): 3230, 3100, 1685, 1640.

NMR (δ, CF$_3$COOH): 8.50 (broad, 1H, N$\underline{H}$), 8.20–7.9 (m, 1H, aromatic), 7.80–7.10 (m, 8H, aromatic), 7.63 (s, 5H, —CH$_2$C$_6$H$_5$).

Mass (m/e): 317 (M+).

Hydrochloride:

M.p. 229°–230° C. (decomp.) (colorless needles) (recrystallized from methanol).

IR$\nu_{max}^{nujol}$ (cm$^{-1}$): 1690.

EXAMPLE 10

0.37 g of 65% sodium hydride are suspended in 15 ml of anhydrous benzene, and a solution of 1.45 g of 1,2,3,4-tetrahydro-1-((N-benzyloxycarbonylamino)methyl)-2-ethyl-β-carboline in 25 ml of anhydrous benzene is added to the suspension at room temperature under stirring. After the mixture is stirred for 30 minutes, said mixture is refluxed for 30 minutes. After cooling, ethyl acetate is added to the reaction mixture. The mixture is washed with water, dried and then evaporated to remove solvent. The residue is recrystallized from benzene, whereby 0.90 g of 1-oxo-4-ethyl-1H-2,3,3a,4,5,6-hexahydro-2,4,10b-triazafluoranthene are obtained as colorless prisms. Yield: 88%.

M.p. 182°–183° C.

IR$\nu_{max}^{nujol}$ (cm$^{-1}$): 3245, 3150, 3125, 1710, 1650.

NMR (δ, CDCl$_3$): 8.20 (m, 1H, aromatic), 7.3 (m, 3H, aromatic), 6.60 (s, 1H, >N$\underline{H}$), 1.13 (t, 3H, J=7 Hz, >N—CH$_2$C$\underline{H}_3$).

Mass (m/e): 255 (M+), 254, 198 (base peak).

Hydrochloride:

M.p. 247.5°–249.5° C. (colorless needles) (recrystallized from methanol).

IR$\nu_{max}^{nujol}$ (cm$^{-1}$): 3250, 2700–2300, 1710.

EXAMPLE 11

0.58 g of 66% sodium hydride are suspended in 20 ml of anhydrous benzene, and a solution of 2.1 g of 1,2,3,4- tetrahydro-1-((N-ethoxycarbonylamino)methyl)-2-n-butyl-β-carboline in 10 ml of anhydrous benzene is added to the suspension. The mixture is refluxed for 40 minutes. After the reaction, a small amount of methanol is added to the reaction mixture, and said mixture is poured into ice-water. The aqueous mixture is extracted with ethyl acetate. The extracts are washed with water, dried and evaporated to remove solvent. The residue (red oil, 1.5 g) is purified by silica gel chromatography (Solvent: ethyl acetate-benzene(1:1)). 0.70 g of 1-oxo-4-n-butyl-1H-2,3,3a,4,5,6-hexahydro-2,4,10b-triazafluoranthene are thereby obtained. Yield: 40.3%.

M.p. 163°–164° C. (pale yellow prisms) (recrystallized from ethyl acetate).

IR$\nu_{max}^{nujol}$ (cm$^{-1}$): 3240, 3110, 1700, 1650.

NMR (δ, CDCl$_3$): 8.45–8.10 (m, 1H, aromatic) 7.55–7.10 (m, 3H, aromatic), 6.40–6.20 (m, 1H, >N$\underline{H}$), 1.9–1.10 (m, 8H), 1.10–0.75 (m, 3H, —(CH$_2$)$_3$C$\underline{H}_3$).

Mass (m/e): 283 (M$^+$).

EXAMPLE 12

To a solution of 200 mg of 1,2,3,4-tetrahydro-1-((N-ethoxycarbonylamino)methyl)-2-n-butyl-β-carboline in 5 ml of toluene are added 183 mg of 1,8-diazabicyclo(5,4,0)undecene-7, and the mixture is refluxed for 48 hours. After the reaction, ethyl acetate is added to the reaction mixture, and said mixture is washed with water, dried and then evaporated to remove solvent. The residue is purified by silica gel chromatography (Solvent: ethyl acetate-benzene (1:1)), and then recrystallized from ethyl acetate. 137 mg of 1-oxo-4-n-butyl-1H-2,3,3a,4,5,6-hexahydro-2,4,10b-triazafluoranthene are thereby obtained. Yield: 80%.

The physico-chemical properties of this product are identical with those of the product obtained in Example 11.

EXAMPLE 13

760 mg of 60% sodium hydride are suspended in 25 ml of anhydrous benzene, and a solution of 2.87 g of 1,2,3,4-tetrahydro-1-(1-(N-ethoxycarbonylamino)ethyl)-β-carboline in 25 ml of anhydrous benzene is added dropwise to the suspension. The mixture is refluxed for 1.5 hours. After cooling, the reaction mixture is evaporated to remove benzene. Ice is added to the residue, and the mixture is extracted with chloroform. The extracts are washed with water, dried and then evaporated to remove solvent. The residue (3 g) thus obtained is purified by silica gel chromatography (Solvent: 1% methanol-chloroform), whereby the following two compounds are obtained.

(A) 1-oxo-3-methyl-4-benzyl-1H-2,3,3a,4,5,6-hexahydro-2,4,10b-triazafluoranthene (trans isomer): Yield: 1.13 g (44.8%).

M.p. 238°–239° C. (colorless needles) (recrystallized from methanol).

IR$\nu_{max}^{nujol}$ (cm$^{-1}$): 3300, 1715, 1670, 1650, 760, 750, 700.

NMR (δ, CDCl$_3$): 8.25 (m, 1H, aromatic), 7.6–7.0 (m, 8H, aromatic), 6.07 (m, 1H, >N$\underline{H}$), 4.2–2.4 (m, 8H), 1.14 (d, 3H, J=6.3 Hz, CHC$\underline{H}_3$).

Mass (m/e): 331 (M$^{30}$), 260, 91 (base peak).
Hydrochloride:

M.p. 197°–200° C. (decomp.) (pale crimson prisms) (recrystallized from ethanol).

IR$\nu_{max}^{nujol}$ (cm$^{-1}$): 3425, 3225, 2600–2300, 1700, 1645, 740, 700.

(B) 1-oxo-3-methyl-4-benzyl-1H-2,3,3a,4,5,6-hexahydro-2,4,10b-triazafluoranthene (cis isomer): Yield: 1.10 g (46.3%).

M.p. 203°–204° C. (colorless needles) (recrystallized from methanol).

IR$\nu_{max}^{nujol}$ (cm$^{-1}$): 3230, 1710, 1635, 745, 700.

NMR (δ, CDCl$_3$): 8.25 (m, 1H, aromatic), 7.6–7.0 (m, 8H, aromatic), 5.67 (s, 1H, >NH), 4.0–2.4 (m, 8H), 1.36 (d, 3H, J=5.4 Hz, >CHC$\underline{H}_3$).

Mass (m/e): 331 (M$^+$), 260, 91 (base peak).
Hydrochloride:

M.p. 190°–192° C. (decomp.) (pale crimson needles) (recrystallized from ethanol).

IR$\nu_{max}^{nujol}$ (cm$^{-1}$): 3400, 3200, 1710, 1645, 755, 700.

EXAMPLE 14

87 mg of 66% sodium hydride are suspended in 5 ml of anhydrous benzene, and a solution of 0.33 g of 1,2,3,4-tetrahydro-1-((N-ethoxycarbonyl-N-methylamino)methyl)-2-n-butyl-β-carboline in 5 ml of anhydrous benzene is added to the suspension at room temperature under stirring. The mixture is refluxed for 2 hours. After the reaction mixture is poured into ice-water, the aqueous mixture is extracted with ethyl acetate. The extracts are washed with water, dried and then evaporated to remove solvent. The residue (0.27 g) is purified by silica gel chromatography (Solvent: chloroform-ethyl acetate(2:1)). 0.15 g of 1-oxo-2-methyl-4-n-butyl-1H-2,3,3a,4,5,6-hexahydro-2,4,10b-triazafluoranthene are thereby obtained as a yellow oil. Yield: 52.6% Said oil is crystallized with n-hexane to give colorless scales melting at 103°–105° C.

EXAMPLE 15

0.5 g of 10% palladium-carbon are added to a solution of 2.0 g of 1-oxo-4-benzyl-1H-2,3,3a,4,5,6-hexahydro-2,4,10b-triazafluoranthene in 30 ml of ethanol-conc. hydrochloric acid (2:1). The mixture is stirred at 40° C. under hydrogen atmosphere. After hydrogen uptake is completed, insoluble materials are removed by filtration. The filtrate is evaporated under reduced pressure to remove solvent. The residue is alkalized with a saturated sodium bicarbonate solution under cooling, and then extracted with chloroform. The extracts are washed with water, dried and then evaporated to remove solvent, whereby 1.30 g of 1-oxo-1H-2,3,3a,4,5,6-hexahydro-2,4,10b-triazafluoranthene are obtained. Yield: 90.9%.

M.p. 211°–214° C. (decomp.) (colorless scales) (recrystallized from methanol).

IR$\nu_{max}^{nujol}$ (cm$^{-1}$): 3250, 3170, 3050, 1670, 1640.

NMR (δ, CF$_3$COOH): 8.20 (m, 1H, aromatic), 7.6–7.3 (m, 3H, aromatic).

Mass (m/e): 227 (M$^+$).
Hydrochloride:

M.p. 266° C. (decomp.) (colorless needles) (recrystallized from water).

IR$\nu_{max}^{nujol}$ (cm$^{-1}$): 3470, 3175, 3125, 2670, 1690, 1680, 1650.

EXAMPLE 16

A mixture of 6.80 g of 1-oxo-2-methyl-4-benzyl-1H-2,3,3a,4,5,6-hexahydro-2,4,10b-triazafluoranthene, 500 ml of methanol, 50 ml of 10% hydrochloric acid and 1.5 g of 10% palladium-carbon is treated in the same manner as described in Example 15. 4.60 g of 1-oxo-2-methyl-1H-2,3,3a,4,5,6-hexahydro-2,4,10b-triazafluoranthene are thereby obtained.

Yield: 92.9%.

M.p. 108°–110° C. (pale red prisms) (recrystallized from ethyl ether).

IR$\nu_{max}^{nujol}$ (cm$^{-1}$): 3550, 3247, 1690, 1645.

NMR (δ, CDCl$_3$): 8.25–8.10 (m, 1H, aromatic), 7.50–7.10 (m, 3H, aromatic), 3.09 (s, 3H, >N—C$\underline{H}_3$), 1.90 (s, 1H, >N$\underline{H}$).

Mass (m/e): 241 (M$^+$).

Hydrochloride:

M.p. 249°–250° C. (decomp.) (pale yellow needles) (recrystallized from a mixture of methanol and ethyl ether).

IR$\nu_{max}^{nujol}$ (cm$^{-1}$): 3450, 2700, 2600, 2525, 2450, 1710(sh), 1690, 1650, 1600.

EXAMPLE 17

A mixture of 13.0 g of 1-oxo-2-ethyl-4-benzyl-1H-2,3,3a,4,5,6-hexahydro-2,4,10b-triazafluoranthene, 1000 ml of methanol, 80 ml of water, 40 ml of 10% hydrochloric acid and 3.0 g of 10% palladium-carbon is shaken at 40° C. for 3 hours under hydrogen atmosphere at 2 atmospheric pressures. After the reaction, the reaction mixture is treated in the same manner as described in Example 15. 8.22 g of 1-oxo-2-ethyl-1H-2,3,3a,4,5,6-hexahydro-2,4,10b-triazafluoranthene are thereby obtained. Yield: 85.6%.

M.p. 139°–140° C. (colorless prisms) (recrystallized from a mixture of benzene and acetone).

IR$\nu_{max}^{nujol}$ (cm$^{-1}$): 3297, 3050, 1690, 1678, 1640.

NMR (δ, CDCl$_3$): 8.20 (m, 1H, aromatic), 7.5–6.9 (m, 3H, aromatic), 1.59 (s, 1H, >N$\underline{H}$), 1.20 (t, 3H, >NCH$_2$C$\underline{H}_3$).

Mass (m/e): 255 (M$^+$).

Hydrochloride:

M.p. 281°–283° C. (decomp.).

IR$\nu_{max}^{nujol}$ (cm$^{-1}$): 3350(br), 2800–2100, 1690, 1645.

EXAMPLE 18

A mixture of 1.2 g of 1-oxo-2-isopropyl-4-benzyl-1H-2,3,3a,4,5,6-hexahydro-2,4,10b-triazafluoranthene, 0.5 g of 10% palladium-carbon, 150 ml of methanol and 20 ml of 10% hydrochloric acid is treated in the same manner as described in Example 15. 0.85 g of 1-oxo-2-isopropyl-1H-2,3,3a,4,5,6-hexahydro-2,4,10b-triazafluoranthene are thereby obtained. Yield: 95.5%.

M.p. 136°–137° C. (colorless needles) (recrystallized from isopropyl ether).

IR$\nu_{max}^{nujol}$ (cm$^{-1}$): 3290, 1690, 1680, 1640.

NMR (δ, CDCl$_3$): 8.33–8.10 (m, 1H, aromatic), 7.5–7.0 (m, 3H, aromatic), 4.82 (m, 1H, —C$\underline{H}$(CH$_3$)$_2$), 1.61 (s, 1H, >N$\underline{H}$), 1.25 (d, 3H, J=7 Hz, —C$\underline{H}_3$), 1.15 (d, 3H, J=7 Hz, —C$\underline{H}_3$).

Mass (m/e): 269 (M$^+$).

Hydrochloride:

M.p. 274° C. (decomp.) (colorless needles) (recrystallized from ethanol).

IR$\nu_{max}^{nujol}$ (cm$^{-1}$): 2750, 2600, 2525, 2425, 1685, 1650.

EXAMPLE 19

A mixture of 3.1 g of 1-oxo-2-n-pentyl-4-benzyl-1H-2,3,3a,4,5,6-hexahydro-2,4,10b-triazafluoranthene, 100 ml of methanol, 20 ml of 10% hydrochloric acid and 1.0 g of 10% palladium-carbon is treated in the same manner as described in Example 15 except that the reaction is carried out at room temperature. 1.90 g of 1-oxo-2-n-pentyl-1H-2,3,3a,4,5,6-hexahydro-2,4,10b-triazafluoranthene are thereby obtained as a yellow oil. Yield: 79.8%.

IR$\nu_{max}^{film}$ (cm$^{-1}$): 3300, 3050, 1690, 1640.

NMR (δ, CDCl$_3$): 8.16 (m, 1H, aromatic), 7.52–7.00 (m, 3H, aromatic), 2.11 (s, 1H, >N$\underline{H}$), 1.84–1.20 (m, 8H), 0.90 (t, 3H, >N(CH$_2$)$_4$C$\underline{H}_3$).

Mass (m/e): 297 (M$^+$).

Hydrochloride:

M.p. 246° C. (d.p. 282° C.).

EXAMPLE 20

A mixture of 2.8 g of 1-oxo-2-ethoxycarbonylmethyl-4-benzyl-1H-2,3,3a,4,5,6-hexahydro-2,4,10b-triazafluoranthene, 300 ml of methanol, 20 ml of 10% hydrochloric acid and 1.0 g of 10% palladium-carbon is treated in the same manner as described in Example 15 except that the reaction is carried out at room temperature. 1.32 g of 1-oxo-2-ethoxycarbonylmethyl-1H-2,3,3a,4,5,6-hexahydro-2,4,10b-triazafluoranthene are thereby obtained. Yield: 60.8%

M.p. 122°–123° C. (pale crimson needles) (recrystallized from isopropyl ether).

IR$\nu_{max}^{nujol}$ (cm$^{-1}$): 3280, 1735, 1690, 1680.

NMR (δ, CDCl$_3$): 8.35–8.0 (m, 1H, aromatic), 7.50–7.10 (m, 3H, aromatic), 4.21 (q, 2H, J=7 Hz, —C$\underline{H}_2$CH$_3$), 1.80 (s, 1H, >N$\underline{H}$), 1.29 (t, 3H, J=7 Hz, —CH$_2$C$\underline{H}_3$).

Mass (m/e): 313 (M$^+$).

Hydrochloride:

M.p. 252°–254° C.(decomp.) (pale yellow needles) (recrystallized from a mixture of ethanol and isopropyl ether).

IR$\nu_{max}^{nujol}$(cm$^{-1}$): 2700–2300, 1740, 1710.

EXAMPLE 21

A mixture of 1.60 g of 1-oxo-2-ethoxyethyl-4-benzyl-1H-2,3,3a,4,5, 6-hexahydro-2,4,10b-triazafluoranthene, 20 ml of methanol, 5 ml of 10% hydrochloric acid and 0.5 g of 10% palladium-carbon is treated in the same manner as described in Example 15 except that the reaction is carried out at room temperature. 0.37 g of 1-oxo-2-ethoxyethyl-1H-2,3,3a,4,5, 6-hexahydro-2,4,10b-triazafluoranthene are thereby obtained as a pale yellow oil. Yield: 30.3%

IR$\nu_{max}^{film}$(cm$^{-1}$): 3550, 3340.

Mass (m/e): 299 (M$^+$).

Rf-value: 0.60 (chloroform-ethyl acetate (4:1), on silica plate).

EXAMPLE 22

A mixture of 1.8 g of 1-oxo-2-(2-tetrahydropyran-2-yl-oxy)ethyl)-4-benzyl-1H-2,3,3a,4,5,6-hexahydro-2,4,10b-triazafluoranthene, 200 ml of methanol and 1.6 g of 10% palladium-carbon is stirred at room temperature under hydrogen atmosphere for 48 hours. After hydrogen uptake is completed, insoluble materials are removed by filtration. The filtrate is evaporated to remove solvent, and the residue is purified by silica gel chromatography (Solvent: chloroform-methanol (10:0.5)). 0.92 g of 1-oxo-2-(2-(tetrahydropyran-2-yl-oxy)ethyl)-1H-2,3,3a,4,5,6-hexahydro-2,4,10b-triazafluoranthene are thereby obtained as a pale red oil.

Yield: 64.3%.

IR$\nu_{max}^{film}$(cm$^{-1}$): 3550, 3300, 3050, 1730, 1680, 1640.

NMR (δ, CDCl$_3$): 8.30–8.10 (m, 1H, aromatic), 7.55–7.10 (m, 3H, aromatic), 4.59

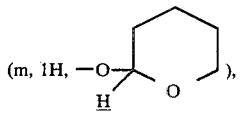

1.90 (s, 1H, >NH), 1.80–1.30 (m, 6H).
Mass (m/e): 355 (M+).

EXAMPLE 23

A mixture of 4.39 g of 1-oxo-2,3-dimethyl-4-benzyl-1H-2,3,3a,4,5, 6-hexahydro-2,4,10b-triazafluoranthene (trans isomer), 200 ml of methanol-water (1:1), 1.5 ml of conc.hydrochloric acid and 800 mg of 10% palladium-carbon is stirred at room temperature under hydrogen atmosphere. After hydrogen uptake is completed, insoluble materials are removed by filtration. The filtrate is condensed, and water is added to the residue. The aqueous mixture is adjusted to pH 11 with potassium carbonate, and then extracted with chloroform. The extracts are washed with a saturated sodium chloride solution, dried and then evaporated to remove solvent. The residue thus obtained is recrystallized from a mixture of n-hexane and ethyl acetate. 3.12 g of 1-oxo-2,3-dimethyl-1H-2,3,3a,4,5,6-hexahydro-2,4,10b-triazafluoranthene (trans isomer) are thereby obtained as colorless needles. Yield: 96.4%

M.p. 94°–96° C.
$IR\nu_{max}^{nujol}$ (cm$^{-1}$): 3200, 1680, 1640, 750.
NMR (δ, CDCl$_3$): 8.20 (m, 1H, aromatic), 7.6–7.0 (m, 3H, aromatic), 3.10 (s, 3H, >N—CH$_3$), 2.53 (broad s, 1H, >NH), 0.99 (d, 3H, J=6.4 Hz, CHCH$_3$).
Mass (m/e): 255 (M+), 170 (base peak).
Hydrochloride:
M.p. 262°–263° C. (decomp.) (colorless granules) (recrystallized from methanol).
$IR\nu_{max}^{nujol}$ (cm$^{-1}$): 2800–2400, 1690, 1650, 765, 750, 730.

EXAMPLE 24

A mixture of 4.40 g of 1-oxo-2,3-dimethyl-4-benzyl-1H-2,3,3a,4,5, 6-hexahydro-2,4,10b-triazafluoranthene (cis isomer), 200 ml of methanol-water (1:1), 1.5 ml of conc.hydrochloric acid and 0.5 g of 10% palladium-carbon is treated in the same manner as described in Example 23. 3.14 g of 1-oxo-2,3-dimethyl- 1H-2,3,3a,4,5,6-hexahydro-2,4,10b-triazafluoranthene (cis iosmer) are thereby obtained as colorless needles. Yield: 97%.

M.p. 165°–166° C.
$IR\nu_{max}^{nujol}$ (cm$^{-1}$): 3260, 1660, 1630, 770, 740
NMR (δ, CDCl$_3$): 8.25 (m, 1H, aromatic), 7.5–7.0 (m, 3H, aromatic), 3.05 (s, 3H, >N—CH$_3$), 1.57 (s, 1H, >NH), 1.43 (d, 3H, J=6.2 Hz, CHCH$_3$).
Mass (m/e): 255 (M+), 170 (base peak).
Hydrochloride:
M.p. 267°–268° C. (decomp.) (colorless needles) (recrystallized from methanol).
$IR\nu_{max}^{nujol}$ (cm$^{-1}$): 2800–2300, 1690, 1645, 760, 755.

EXAMPLE 25

0.4 g of 66% sodium hydride are suspended in 30 ml of anhydrous tetrahydrofuran, and a solution of 2.41 g of 1-oxo-2-methyl-1H-2,3,3a,4,5, 6-hexahydro-2,4,10b-triazafluoranthene in 20 ml of anhydrous tetrahydrofuran is added to the suspension. The mixture is stirred at room temperature under nitrogen atmosphere for one hour, and then heated at 45° C. with stirring for one hour. After the mixture is cooled to 20° C., a solution of 1.70 g of methyl iodide in 5 ml of anhydrous tetrahydrofuran is added dropwise thereto. Then, the mixture is stirred at room temperature for 3 hours, and further stirred at 40°–45° C. for 2 hours. After the reaction mixture is condensed under reduced pressure to remove solvent, water is added to the residue. The aqueous mixture is extracted with ethyl acetate. The extracts are washed with water, dried and then evaporated to remove solvent. The residue (red oil, 1.89 g) thus obtained is purified by silica gel chromatography (Solvent: chloroform-ethyl acetate (2:1)), and then recrystallized from isopropyl ether. 0.95 g of 1-oxo-2,4-dimethyl-1H-2,3, 3a,4,5,6-hexahydro-2,4,10b-triazafluoranthene are thereby obtained as colorless needles. Yield: 37.3%.

M.p. 117°–118° C.
$IR\nu_{max}^{nujol}$ (cm$^{-1}$): 1690, 1650.
NMR (δ, CDCl$_3$): 3.11 (s, 3H, CO—N—CH$_3$), 2.41(s, 3H, >N—CH$_3$).
Mass (m/e): 255 (M+).
Hydrochloride:
M.p. 238° C. (decomp.) (pale yellow prisms) (recrystallized from ethanol).
$IR\nu_{max}^{nujol}$ (cm$^{-1}$): 2600–2000, 1695, 1647, 1495.

EXAMPLE 26

0.40 g of 66% sodium hydride are suspended in 20 ml of anhydrous tetrahydrofuran, and a solution of 2.41 g of 1-oxo-2-methyl-1H-2,3,3a,4,5,6-hexahydro-2,4,10b-triazafluoranthene in 20 ml of anhydrous tetrahydrofuran is added to the suspension. The mixture is stirred at room temperature under nitrogen atmosphere for one hour, and further stirred at 45° C. for one hour. After the mixture is cooled to 20° C., 1.9 g of ethyl iodide are added thereto. The mixture is treated in the same manner as described in Example 25. 1.52 g of 1-oxo-2-methyl-4-ethyl-1H-2,3,3a,4,5,6-hexahydro-2,4,10b-triazafluoranthene are thereby obtained as an oil. Yield: 56.0%.

$IR\nu_{max}^{film}$ (cm$^{-1}$): 1710, 1695, 1650.
NMR (δ, CDCl$_3$): 8.4–8.1 (m, 1H, aromatic), 7.55–7.10 (m, 3H, aromatic), 3.15 (s, 3H, >N—CH$_3$), 1.16 (t, 3H, J=7 Hz, —CH$_2$CH$_3$).
Mass (m/e): 269 (M+).
Hydrochloride:
M.p. 249° C. (decomp.) (melting at 291° C.) (colorless powder) (recrystallized from ethanol).
$IR\nu_{max}^{nujol}$ (cm$^{-1}$): 2600–2000, 1690, 1640, 1495.

EXAMPLE 27

To a solution of 1.20 g of 1-oxo-2-methyl-1H-2,3,3a,4,5,6-hexahydro-2,4,10b-triazafluoranthene in 15 ml of dimethylformamide are added 1.11 g of n-propyl iodide and 1.04 g of anhydrous potassium carbonate, and the mixture is stirred at room temperature for 67 hours. After the reaction, ethyl acetate is added to the reaction mixture, and said mixture is washed with water, dried and then evaporated to remove solvent. The residue (reddish yellow oil, 1.3 g) thus obtained is purified by silica gel chromatography (Solvent: chloroform-ethyl acetate (3:2)), and then recrystallized from isopropyl ether. 1.30 g of 1-oxo-2-methyl-4-n-propyl-1H-2,3,3a,4,5,6-hexahydro-2,4,10b-triazafluoranthene are thereby obtained as pale green prisms. Yield: 92.2%.

M.p. 129°–130° C.
$IR\nu_{max}^{nujol}$ (cm$^{-1}$): 1690, 1646
NMR (δ, CDCl$_3$): 8.22 (m, 1H, aromatic), 7.60 (m, 3H, aromatic), 3.11 (s, 3H, N CH$_3$), 2.40 (t, 2H, >NCH₂CH₂CH₃), 1.60 (m, 2H, >NCH₂C$\underline{H}$₂CH₃), 0.90 (t, 3H, >NCH₂CH₂C$\underline{H}$₃).

Mass (m/e): 283 (M+).

Hydrochloride:

M.p. 241°–241.5° C. (decomp.) (colorless scales) (recrystallized from a mixture of ethanol and isopropyl ether).

IR$\nu_{max}^{nujol}$ (cm$^{-1}$): 2600–2000, 1690, 1645, 1480.

EXAMPLE 28

A mixture of 1.20 g of 1-oxo-2-methyl-1H-2,3,3a,4,5,6-hexahydro-2,4,10b-triazafluoranthene, 15 ml of dimethylformamide, 1.09 g of isopropyl iodide and 1.04 g of anhydrous potassium carbonate is treated in the same manner as described in Example 27. 0.4 g of 1-oxo-2-methyl-4-isopropyl-1H-2,3,3a,4,5,6-hexahydro-2,4,10b-triazafluoranthene are thereby obtained. Yield: 28.3%.

M.p. 131°–133° C. (colorless prisms) (recrystallized from isopropyl ether).

IR$\nu_{max}^{nujol}$ (cm$^{-1}$): 1680, 1640.

NMR (δ, CDCl₃): 3.10 (s, 3H, >N—C$\underline{H}$₃), 1.18, 1.03 (d,d, 3H, >N—CH(C$\underline{H}$₃)₂).

Mass (m/e): 283 (M+).

Hydrochloride:

M.p. 210°–212° (decomp.) (colorless prisms) (recrystallized from ethanol).

IR$\nu_{max}^{nujol}$ (cm$^{-1}$): 2700–2000, 1690, 1642, 1485, 1350, 1340.

EXAMPLE 29

A mixture of 2.7 g of 1-oxo-2-methyl-1H-2,3,3a,4,5,6-hexahydro-2,4,10b-triazafluoranthene, 30 ml of dimethylformamide, 2.63 g of n-butyl iodide and 2.3 g of anhydrous potassium carbonate is heated at 50° C. with stirring under nitrogen atmosphere for 20 hours. After the reaction, the reaction mixture is treated in the same manner as described in Example 27. 2.93 g of 1-oxo-2-methyl-4-n-butyl-1H-2,3,3a,4,5,6-hexahydro-2,4,10b-triazafluoranthene are thereby obtained. Yield: 88.1%.

M.p. 104°–105° C. (colorless scales) (recrystallized from a mixture of isopropyl ether and n-hexane).

IR$\nu_{max}^{nujol}$ (cm$^{-1}$): 1695, 1650, 1485.

NMR (δ, CDCl₃): 8.4–8.1 (m, 1H, aromatic), 7.5–7.1 (m, 3H, aromatic), 3.13 (s, 3H, >N—C$\underline{H}$₃), 1.80–0.80 (m, 9H, —(C$\underline{H}$₂)₃C$\underline{H}$₃).

Mass (m/e): 297 (M+).

Hydrochloride:

M.p. 228°–230° (decomp.) (pale yellow prisms) (recrystallized from a mixture of isopropyl ether and methanol).

IR$\nu_{max}^{nujol}$ (cm$^{-1}$): 2600–2000, 1708, 1643, 1500.

Methanesulfonate:

M.p. 177°–179° (colorless prisms) (recrystallized from a mixture of ethanol and ether).

IR$\nu_{max}^{nujol}$ (cm$^{-1}$): 2700–2100, 1700, 1650, 1500.

EXAMPLE 30

A mixture of 1.3 g of 1-oxo-2-methyl-1H-2,3,3a,4,5,6-hexahydro-2,4,10b-triazafluoranthene, 15 ml of dimethylformamide, 0.89 g of isobutyl bromide and 1.04 g of anhydrous potassium carbonate is stirred at room temperature for 20 hours, and then heated at 50° C. with stirring for 3 days. After the reaction, the reaction mixture is treated in the same manner as described in Example 27. 0.591 g of 1-oxo-2-methyl-4-isobutyl-1H-2,3,3a,4,5,6-hexahydro-2,4,10b-triazafluoranthene are thereby obtained. Yield: 36.9%.

M.p. 150°–153° C. (colorless needles) (recrystallized from n-hexane).

IR$\nu_{max}^{nujol}$ (cm$^{-1}$): 1690, 1640, 1483.

NMR (δ, CDCl₃): 8.3–8.10 (m, 1H, aromatic), 7.5–7.15 (m, 3H, aromatic), 3.10 (s, 3H, >N—C$\underline{H}$₃), 0.91 (d, 6H, CH₂CH(C$\underline{H}$₃)₂).

Mass (m/e): 297 (M+).

Hydrochloride:

M.p. 271° C. (decomp.) (contracting at 230° C.).

IR$\nu_{max}^{nujol}$ (cm$^{-1}$): 2700–2100, 1705, 1655, 1500.

EXAMPLE 31

A mixture of 1.2 g of 1-oxo-2-methyl-1H-2,3,3a,4,5,6-hexahydro-2,4, 10b-triazafluoranthene, 15 ml of dimethylformamide, 1.29 g of n-pentyl iodide and 1.04 g of anhydrous potassium carbonate is stirred at room temperature for 91 hours. After the reaction, the reaction mixture is treated in the same manner as described in Example 27. 0.859 g of 1-oxo-2-methyl-4-n-pentyl-1H-2,3,3a,4,5,6-hexahydro-2,4,10b-triazafluoranthene are thereby obtained. Yield: 55.5%.

M.p. 87°–88° C. (colorless needles) (recrystallized from isopropyl ether).

IR$\nu_{max}^{nujol}$ (cm$^{-1}$): 1690, 1650, 1482.

NMR (δ, CDCl₃): 8.35–8.10 (m, 1H, aromatic), 7.55–7.10 (m, 3H, aromatic), 3.11 (s, 3H, >NC$\underline{H}$₃), 1.74–1.10 (m, 8H), 0.90 (t, 3H, >N(CH₂)₄C$\underline{H}$₃).

Mass (m/e): 311 (M+).

Hydrochloride:

M.p. 183°–200° C. (colorless needles) (recrystallized from a mixture of ethanol and ether).

IR$\nu_{max}^{nujol}$ (cm$^{-1}$): 2600–2200, 1710, 1690, 1642.

EXAMPLE 32

A mixture of 1.2 g of 1-oxo-2-methy-1H-2,3,3a,4,5,6-hexahydro-2,4,10b-triazafluoranthene, 15 ml of dimethylformamide, 1.29 g of isopentyl iodide and 1.04 g of anhydrous potassium carbonate is stirred at room temperature for 97 hours. After the reaction, the reaction mixture is treated in the same manner as described in Example 27. 0.91 g of 1-oxo-2-methyl-4-isopentyl-1H-2,3,3a,4,5,6-hexahydro-2,4,10b-triazafluoranthene are thereby obtained. Yield: 58.7%.

M.p. 92°–93° C. (colorless needles) (recrystallized from isopropyl ether).

IR$\nu_{max}^{nujol}$ (cm$^{-1}$): 1690, 1643.

NMR (δ, CDCl₃): 8.25–8.10 (m, 1H, aromatic), 7.50–7.10 (m, 3H, aromatic), 3.15 (s, 3H, >NC$\underline{H}$₃), 0.90 (d, 6H, >N(CH₂)₂CH(C$\underline{H}$₃)₂).

Mass (m/e): 311 (M+).

Hydrochloride:

M.p. 220°–222° C. (colorless needles) (recrystallized from a mixture of ethanol and isopropyl ether).

IR$\nu_{max}^{nujol}$ (cm$^{-1}$): 2230, 1703, 1642.

EXAMPLE 33

A mixture of 1.20 g of 1-oxo-2-methyl-1H-2,3,3a,4,5,6-hexahydro-2,4, 10b-triazafluoranthene, 20 ml anhydrous acetonitrile, 0.89 g of 2-isopentenyl bromide and 0.9 g of anhydrous potassium carbonate is stirred at room temperature for 20 hours. After the reaction mixture is condensed under reduced pressure, water is added to the residue. The aqueous mixture is extracted with chloroform. The extracts are washed with water, dried and then evaporated to remove solvent. The red oil (1.42 g) thus obtained is purified by silica gel chromatography (Solvent: chloroformethyl acetate(1:1)). 1.0 g of 1-oxo-2-methyl-4-(2-isopentenyl)-

1H-2,3,3a,4,5,6-hexahydro-2,4,10b-triazafluoranthene is thereby obtained as an oil. Yield: 64.9%.

IR$\nu_{max}^{film}$ (cm$^{-1}$): 1690, 1642.

NMR (δ, CDCl$_3$): 8.30-8.10 (m, 1H, aromatic), 7.50-7.10 (m, 3H, aromatic), 3.12 (s, 3H, >N—CH$_3$), 1.78, 1.71 (s,s, 3H, 3H, —CH$_2$CH=C(CH$_3$)$_2$).

Mass (m/e): 309 (M+).

Hydrochloride:

M.p. 217° C. (decomp.) (colorless scales) (recrystallized from a mixture of ethanol and isopropyl ether).

IR$\nu_{max}^{nujol}$(cm$^{-1}$): 2700-2100, 1703, 1650, 1490.

EXAMPLE 34

A mixture of 1.0 g of 1-oxo-2-methyl-1H-2,3,3a,4,5,6-hexahydro-2,4,10b-triazafluoranthene, 10 ml of dimethylformamide, 0.94 g of cyclohexylmethyl bromide and 0.86 g of anhydrous potassium carbonate is stirred at room temperature for 12 days, and then heated at 60° C. with stirring for 2 days. After the reaction, the reaction mixture is treated in the same manner as described in Example 27. 400 mg of 1-oxo-2-methyl-4-cyclohexylmethyl-1H-2,3,3a,4,5,6-hexahydro-2,4,10b-triazafluoranthene are thereby obtained as a pale yellow oil. Yield: 28.9%.

IR$\nu_{max}^{liq.}$ (cm$^{-1}$): 1700 (sh), 1690, 1640, 1600, 1480.

NMR (δ, CDCl$_3$): 8.3-8.1 (m, 1H, aromatic), 7.5-7.05 (m, 3H, aromatic), 3.10 (s, 3H, >N—CH$_3$), 1.90-0.6 (m, 13H).

Mass (m/e): 337 (M+).

Hydrochloride:

M.p. 204°-206° C. (decomp.) (brown fine needles) (recrystallized from ethanol).

IR$\nu_{max}^{nujol}$ (cm$^{-1}$): 2400, 1710, 1642.

EXAMPLE 35

A mixture of 1.20 g of 1-oxo-2-methyl-1H-2,3,3a,4,5,6-hexahydro-2,4, 10b-triazafluoranthene, 20 ml of dimethylformamide, 1.0 g of benzyl bromide and 1.10 g of anhydrous potassium carbonate is treated in the same manner as described in Example 27. 1.26 g of 1-oxo-2-methyl-4-benzyl-1H-2,3,3a,4,5,6-hexahydro-2,4,10b-triazafluoranthene are thereby obtained. Yield: 82.0%.

M.p. 173°-174° C. (colorless prisms) (recrystallized from methanol).

IR$\nu_{max}^{nujol}$ (cm$^{-1}$): 1685, 1635.

NMR (δ, CDCl$_3$): 8.30 (m, 1H, aromatic), 7.27 (s, 5H, —CH$_2$—C$_6$H$_5$), 3.50 (s, 2H, —CH$_2$—C$_6$H$_5$), 3.08 (s, 3H, >N—CH$_3$).

Mass (m/e): 331 (M+).

Hydrochloride:

M.p. 241° C. (decomp.) (colorless needles) (recrystallized from methanol).

IR$\nu_{max}^{nujol}$ (cm$^{-1}$): 2600-2000, 1710, 1650, 1600, 1490.

EXAMPLE 36

A mixture of 1.0 g of 1-oxo-2-methyl-1H-2,3,3a,4,5,6-hexahydro-2,4,10b-triazafluoranthene, 10 ml of dimethylformamide, 0.98 g of phenethyl bromide and 0.86 g of anhydrous potassium carbonate is treated in the same manner as described in Example 27. The crude product thus obtained is recrystallized from isopropyl ether, whereby 0.8 g of 1-oxo-2-methyl-4-phenethyl-1H-2,3,3a,4,5,6-hexahydro-2,4,10b-triazafluoranthene are obtained as pale yellow prisms. Yield: 56.7%.

M.p. 136°-137° C.

IR$\nu_{max}^{nujol}$ (cm$^{-1}$): 1683, 1643, 1600, 1490.

NMR (δ, CDCl$_3$): 8.40-8.10 (m, 1H, aromatic), 7.50-7.00 (m, 8H, aromatic).

Mass (m/e): 345 (M+).

Methanesulfonate:

M.p. 224°-224.5° C. (colorless prisms) (recrystallized from ethanol).

IR$\nu_{max}^{nujol}$ (cm$^{-1}$): 3600-3300, 2800-2100, 1700, 1650, 1600, 1490.

EXAMPLE 37

A mixture of 1.30 g of 1-oxo-2-ethyl-1H-2,3,3a,4,5,6-hexahydro-2, 4,10b-triazafluoranthene, 220 mg of 66% sodium hydride, 1.0 g of benzyl bromide and 25 ml of tetrahydrofuran is treated in the same manner as described in Example 25. 1.19 g of 1-oxo-2-ethyl-4-benzyl-1H-2,3,3a,4,5,6-hexahydro-2,4,10b-triazafluoranthene are thereby obtained. Yield: 70.0%.

M.p. 135°-135.5° C. (colorless prisms) (recrystallized from ethanol).

IR$\nu_{max}^{nujol}$ (cm$^{-1}$): 1690, 1655.

NMR (δ, CDCl$_3$): 8.30-8.10 (m, 1H, aromatic), 7.50-7.05 (m, 8H, aromatic), 3.60 (q, 2H, J=8.0 Hz, >NCH$_2$CH$_3$), 1.20 (t, 3H, J=8.0 Hz, >NCH$_2$CH$_3$).

Mass (m/e): 345 (M+).

Hydrochloride:

M.p. 222° C. (decomp.) (colorless prisms) (recrystallized from methanol).

IR$\nu_{max}^{nujol}$ (cm$^{-1}$): 2120, 1680, 1645.

EXAMPLE 38

A mixture of 1.33 g of 1-oxo-2-ethyl-1H-2,3,3a,4,5,6-hexahydro-2, 4,10b-triazafluoranthene, 890 mg of methyl iodide, 230 mg of 60% sodium hydride and 40 ml of anhydrous tetrahydrofuran is treated in the same manner as described in Example 25. 1.12 g of 1-oxo-2-ethyl-4-methyl-1H-2,3,3a,4,5,6-hexahydro-2, 4,10b-triazafluoranthene are thereby obtained. Yield: 79.6%.

M.p. 114°-115° C. (colorless needles) (recrystallized from isoproypl ether).

IR$\nu_{max}^{nujol}$ (cm$^{-1}$): 1690, 1650, 1480, 1460, 760.

NMR (δ, CDCl$_3$): 8.25 (m, 1H, aromatic), 7.6-7.1 (m, 3H, aromatic), 2.47 (s, 3H, >N—CH$_3$), 1.23 (t, 3H, J=7 Hz, >N—CH$_2$CH$_3$).

Mass (m/e): 269 (M+), 226 (base peak).

Hydrochloride:

M.p. 248°-250° C. (decomp.) (colorless prisms) (recrystallized from ethanol).

IR$\nu_{max}^{nujol}$ (cm$^{-1}$): 2600-2000, 1700, 1640, 1460, 765.

EXAMPLE 39

A mixture of 1.30 g of 1-oxo-2-ethyl-1H-2,3,3a,4,5,6-hexahydro-2,4,10b-triazafluoranthene, 220 mg of 66% sodium hydride, 936 mg of ethyl iodide and 25 ml of anhydrous tetrahydrofuran is treated in the same manner as described in Example 25. 0.75 g of 1-oxo-2,4-diethyl-1H-2,3,3a,4,5,6-hexahydro-2,4,10b-triazafluoranthene are thereby obtained. Yield: 53.2%.

M.p. 93°-94° C. (pale yellow scales) (recrystallized from isopropyl ether).

IR$\nu_{max}^{nujol}$ (cm$^{-1}$): 1690, 1650.

NMR (δ, CDCl$_3$): 1.22

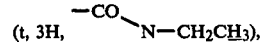

(t, 3H, —CO—N—CH$_2$CH$_3$), 1.18 (t, 3H, >N—CH$_2$CH$_3$).

Mass (m/e): 283 (M+).

Hydrochloride:

M.p. 217°–223° C. (pale brown scales) (recrystallized from a mixture of ethanol and isopropyl ether).

IR$\nu_{max}^{nujol}$ (cm$^{-1}$): 2600–2000, 1685, 1645, 1600.

EXAMPLE 40

A mixture of 1.30 g of 1-oxo-2-ethyl-1H-2,3,3a,4,5,6-hexahydro-2,4,10b-triazafluoranthene, 1.02 g of n-propyl iodide, 0.22 g of 66% sodium hydride and 30 ml of anhydrous tetrahydrofuran is treated in the same manner as described in Example 25. The crude product thus obtained is purified by silica gel chromatography (Solvent: ethyl acetatechloroform(1:4)). 0.53 g of 1-oxo-2-ethyl-4-n-propyl-1H-1,2,3,3a,4,5,6-hexahydro-2,4,10b-triazafluoranthene are thereby obtained as a red oil. Yield: 35.6%

IR$\nu_{max}^{film}$ (cm$^{-1}$): 1730, 1690, 1641, 1600, 1480.

NMR ($\delta$, CDCl$_3$): 8.30–8.1 (m, 1H, aromatic) 7.50–7.10 (m, 3H, aromatic), 2.50 (t, 2H, >N—CH$_2$CH$_2$CH$_3$), 1.60 (sixtet, 2H, >N—CH$_2$C$\underline{H}_2$CH$_3$), 0.95 (t, 3H, >N—CH$_2$CH$_2$C$\underline{H}_3$).

Mass (m/e): 298 (M$^+$ +1).

Rf-value: 0.85 (on silica gel plate, chloroformmethanol (10:1)).

Hydrochloride:

M.p. 267° C. (decomp.) (needles) (recrystallized from a mixture of ethanol and isopropyl ether).

IR$\nu_{max}^{nujol}$ (cm$^{-1}$): 2500–2000, 1685, 1640, 1600, 1480.

EXAMPLE 41

A mixture of 1.30 g of 1-oxo-2-ethyl-1H-2,3,3a,4,5,6-hexahydro-2,4,10b-triazafluoranthene, 0.891 g of n-butyl bromide, 1.04 g of anhydrous potassium carbonate and 18 ml of dimethylformamide is treated in the same manner as described in Example 27. The crude product thus obtained is purified by silica gel chromatography (Solvent: ethyl acetate-chloroform(1:4)). 1.2 g of 1-oxo-2-ethyl-4-n-butyl-1H-2,3,3a,4,5,6-hexahydro-2,4,10b-triazafluoranthene are thereby obtained as a yellow oil. Yield: 76.9%.

IR$\nu_{max}^{film}$ (cm$^{-1}$): 1690, 1650, 1480, 1430.

NMR ($\delta$, CDCl$_3$): 1.21 (t, 3H, >N—CH$_2$C$\underline{H}_3$), 1.90–0.80 (m, 11H).

Rf-value: 0.65 (on silica gel plate, chloroform-ethyl acetate (1:1)).

Hydrochloride:

M.p. 207°–208° C. (pale yellow scales) (recrystallized from a mixture of ethanol and isopropyl ether).

IR$\nu_{max}^{nujol}$ (cm$^{-1}$): 2500, 2400, 2150, 1690, 1640, 1600, 1490.

EXAMPLE 42

A mixture of 1.30 g of 1-oxo-2-ethyl-1H-2,3,3a,4,5,6-hexahydro-2,4,10b-triazafluoranthene, 1.29 g of n-pentyl iodide, 1.04 g of anhydrous potassium carbonate and 15 ml of dimethylformamide is treated in the same manner as described in Example 27. The crude product thus obtained is purified by silica gel chromatography (Solvent: methanolchloroform(1:10)). 1.2 g of 1-oxo-2-ethyl-4-n-pentyl-1H-2,3,3a,4,5,6-hexahydro-2,4,10b-triazafluoranthene are thereby obtained as a pale yellow oil. Yield: 74.1%

IR$\nu_{max}^{film}$ (cm$^{-1}$): 1700(sh), 1690, 1642.

NMR ($\delta$, CDCl$_3$): 4.0–0.80 (m, 27H), 1.23 (t, 3H, >N—CH$_2$C$\underline{H}_3$).

Rf-value: 0.80 (silica gel plate, methanol-chloroform(1:9)).

Methanesulfonate:

M.p. 208.5°–209.5° (pale green prisms) (recrystallized from a mixture of ethanol and isopropyl ether).

IR $\nu_{max}^{nujol}$ (cm$^{-1}$): 2750–2200, 1700, 1680(sh), 1645, 1450.

EXAMPLE 43

A mixture of 0.60 g of 1-oxo-2-isopropyl-1H-2,3,3a,4,5,6-hexahydro-2,4,10b-triazafluoranthene, 0.534 g of n-butyl iodide, 0.456 g of anhydrous potassium carbonate and 10 ml of dimethylformamide is treated in the same manner as described in Example 27. The crude product thus obtained is purified by silica gel chromatography (Solvent: chloroform-ethyl acetate(9:1)). 470 mg of 1-oxo-2-isopropyl-4-n-butyl-1H-2,3,3a,4,5,6-hexahydro-2,4,10b-triazafluoranthene are thereby obtained as a yellow oil. Yield: 65.6%.

IR $\nu_{max}^{film}$ (cm$^{-1}$): 1700, 1690, 1642.

NMR ($\delta$, CDCl$_3$): 8.45–8.10 (m, 1H, aromatic), 7.50–7.10 (m, 3H, aromatic), 4.90 (m, 1H, N—C$\underline{H}$(CH$_3$)$_2$), 1.25, 1.20 (d,d, 3H, 3H, J=7 Hz, 7 Hz, >N—CH (C$\underline{H}_3$)$_2$), 0.98 (m, 3H, >N—(CH$_2$)$_3$—C$\underline{H}_3$).

Mass (m/e): 325 (M$^+$).

Hydrochloride:

M.p. 208°–210° C. (colorless needles) (recrystallized from a mixture of ethanol and isopropyl ether).

IR $\nu_{max}^{nujol}$ (cm$^{-1}$): 2500, 2280, 1690, 1655.

EXAMPLE 44

A mixture of 1.7 g of 1-oxo-2-n-pentyl-1H-2,3,3a,4,5,6-hexahydro-2,4,10b-triazafluoranthene, 1.36 g of n-butyl iodide, 1.18 g of anhydrous potassium carbonate and 20 ml of dimethylformamide is treated in the same manner as described in Example 27. The crude product (red oil, 1.9 g) is purified by silica gel chromatography (Solvent: n-hexane-ethyl acetate (2:1)). 1.69 g of 1-oxo-2-n-pentyl-4-n-butyl-1H-2,3,3a,4,5,6-hexahydro-2,4,10b-triazafluoranthene are thereby obtained as an oil. Yield: 84.1%

IR $\nu_{max}^{film}$ (cm$^{-1}$): 1690, 1645, 1600, 1480.

NMR ($\delta$, CDCl$_3$): 8.30–8.10 (m, 1H, aromatic), 7.50–7.05 (m, 3H, aromatic), 1.90–1.10 (m, 14H), 0.92, 0.90 (s, s, 3H×2).

Hydrochloride:

M.p. 131°–134° C. (colorless fine needles) (recrystallized from a mixture of ethanol and isopropyl ether).

IR$\nu_{max}^{nujol}$ (cm$^{-1}$): 2750–2300, 1690, 1643.

EXAMPLE 45

A mixture of 1.0 g of 1-oxo-2-ethoxycarbonylmethyl-1H-2,3,3a,4,5,6-hexahydro-2, 4,10b-triazafluoranthene, 0.76 g of n-butyl iodide, 0.66 g of anhydrous potassium carbonate and 30 ml of dimethylformamide is treated in the same manner as described in Example 27. The crude product thus obtained is purified by silica gel chromatography (Solvent: chloroform-ethyl acetate (5:1)). 720 mg of 1-oxo-2-ethoxycarbonylmethyl-4-n-butyl-1H-2,3,3a, 4,5,6-hexahydro-2,4,10b-triazafluoranthene are thereby obtained. Yield : 61.0%

M.p. 96°–97° C. (colorless needles) (recrystallized from isopropyl ether).

IR$\nu_{max}^{nujol}$ (cm$^{-1}$): 1738, 1700, 1650.

NMR ($\delta$, CDCl$_3$): 8.30–8.00 (m, 1H, aromatic), 7.50–7.05 (m, 3H, aromatic), 4.25 (s, 2H, >N—C$\underline{H}_2$COOC$_2$H$_5$), 4.18 (q, 2H, J=7 Hz, —C$\underline{H}_2$CH$_3$), 1.25 (t, 3H, J=7 Hz, —CH$_2$C$\underline{H}_3$), 1.10 0.78 (m, 3H, N—(CH$_2$)$_3$—C$\underline{H}_3$).

Mass (m/e): 369 (M$^+$).

Hydrochloride:
M.p. 191°–192° C. (pale yellow powder) (recrystallized from a mixture of ethanol and isopropyl ether).
IR$\nu_{max}^{nujol}$ (cm$^{-1}$): 2600, 2380, 2330, 1738, 1705, 1650.

EXAMPLE 46

A mixture of 0.37 g of 1-oxo-2-(2-ethoxyethyl)-1H-2,3,3a,4,5,6-hexahydro-2,4,10b-triazafluoranthene, 0.29 g of n-butyl iodide, 0.25 g of anhydrous potassium carbonate and 5 ml of dimethylformamide is treated in the same manner as described in Example 27. 223 mg of 1-oxo-2-(2-ethoxyethyl)-4-n-butyl-1H-2,3,3a,4,5,6-hexahydro-2,4,10b-triazafluoranthene are thereby obtained as a red oil. Yield: 52.3%.

IR$\nu_{max}^{film}$ (cm$^{-1}$): 1685, 1643.

NMR ($\delta$, CDCl$_3$): 8.30–8.10 (m, 1H, aromatic), 7.50–7.10 (m, 3H, aromatic), 3.50 (q, 2H, J=7.5 Hz, —OC$\underline{H}_2$CH$_3$), 1.20 (t, 3H, J=7.5 Hz, —OCH$_2$—C$\underline{H}_3$).

Mass (m/e): 355 (M+).
Hydrochloride:
M.p. 190°–196° C. (colorless needles) (recrystallized from a mixture of ethanol and isopropyl ether).
IR$\nu_{max}^{nujol}$ (cm$^{-1}$): 2500–2000, 1680, 1650, 1600, 1490.

EXAMPLE 47

(1) A mixture of 0.92 g of 1-oxo-2-(2-(tetrahydropyran-2-yl-oxy)ethyl)-1H- 2,3,3a,4,5,6-hexahydro-2,4,10b-triazafluoranthene, 0.62 g of n-butyl iodide, 0.54 g of anhydrous potassium carbonate and 10 ml of dimethylformamide is treated in the same manner as described in Example 27. The crude product thus obtained is purified by silica gel chromatography (Solvent: chloroform-methanol (10:1). 0.93 g of 1-oxo-2-(2-(tetrahydropyran-2-yl-oxy)ethyl)-4-n-butyl-1H-2,3,3a,4,5,6-hexahydro-2,4,10b-triazafluorathene are thereby obtained as an oil. Yield: 90.3%

(2) 25 ml of ethanol, 25 ml of water and 2 ml of conc. hydrochloric acid are added to the product obtained in paragraph (1), and the mixture is stirred at room temperature for 26 hours. After the reaction, the reaction mixture is condensed. The residue is alkalized with sodium carbonate, and then extracted with ethyl acetate. The extracts are washed with water, dried and then evaporated to remove solvent. The residue thus obtained is purified by silica gel chromatography (Solvent: ethyl acetate). 600 mg of 1-oxo-2-(2-hydroxyethyl)-4-n-butyl-1H-2,3,3a,4,5,6-hexahydro-2,4,10-triazafluoranthene are thereby obtained as an oil. Yield: 82.2%

IR$\nu_{max}^{film}$ (cm$^{-1}$): 3450, 1690, 1650.

NMR ($\delta$, CDCl$_3$): 3.07 (s, 1H, —O$\underline{H}$), 1.7–1.1 (m, 6H, >N—(C$\underline{H}_2$)$_3$—CH$_3$), 0.94 (m, 3H, >N—(CH$_2$)$_3$—C$\underline{H}_3$).
Hydrochloride:
M.p. 199°–202° C. (colorless fine needles) (recrystallized from ethanol).
IR$\nu_{max}^{nujol}$ (cm$^{-1}$): 3360, 2700–2200, 1695, 1660.

EXAMPLE 48

To a solution of 500 mg of 1-oxo-2,3-dimethyl-1H-2,3,3a,4,5,6-hexahydro-2,4,10b-triazafluoranthene (trans isomer) in 20 ml of acetonitrile are added 350 mg of anhydrous potassium carbonate and 400 mg of ethyl iodide. The mixture is stirred at room temperature for 24 hours, and then refluxed for 24 hours. After the reaction, the reaction mixture is evaporated to remove solvent. Water is added to the residue, and the aqueous mixture is extracted with chloroform. The extracts are washed with water, dried and then evaporated to remove solvent. The residue is purified by silica gel chromatography (Solvent: 0.5% methanol-chloroform). 400 mg of 1-oxo-2,3-dimethyl-4-ethyl- 1H-2,3,3a, 4,5,6-hexahydro-2,4,10b-triazafluoranthene (trans isomer) are thereby obtained. Yield: 61.7%

M.p. 141°–142° C. (colorless plates) (recrystallized from isopropyl ether).

IR$\nu_{max}^{nujol}$ (cm$^{-1}$): 1690, 1640, 770, 760.

NMR ($\delta$, CDCl$_3$): 8.2 (m, 1H, aromatic), 7.6–7.0 (m, 3H, aromatic), 3.12 (s, 3H, >N—C$\underline{H}_3$), 1.16 (t, 3H, J=7.1 Hz, >N—CH$_2$C$\underline{H}_3$), 0.98 (d, 3H, J=6.3 Hz, >CH—C$\underline{H}_3$).

Mass (m/e): 283 (M+), 198 (base peak).
Hydrochloride:
M.p. 245°–247° C. (colorless granules) (recrystallized from methanol).
IR$\nu_{max}^{nujol}$ (cm$^{-1}$): 3500, 3400, 1690, 1645, 770, 740.

EXAMPLE 49

A mixture of 1.35 g of 1-oxo-2,3-dimethyl-1H-2,3,3a,4,5,6-hexahydro-2,4,10b-triazafluoranthene (cis isomer), 1.25 g of ethyl iodide, 1.10 g of anhydrous potassium carbonate and 40 ml of acetonitrile is treated in the same manner as described in Example 48. 1.2 g of 1-oxo-2,3,-dimethyl-4-ethyl-1H-2,3,3a,4,5,6-hexahydro-2,4,10b-triazafluoranthene (cis isomer) are thereby obtained. Yield: 80%.

M.p. 118°–119° C. (colorless needles) (recrystallized from isopropyl ether).

IR$\nu_{max}^{nujol}$ (cm$^{-1}$): 1680, 1635, 750.

NMR ($\delta$, CDCl$_3$): 8.3 (m, 1H, aromatic), 7.6–6.9 (m, 3H, aromatic), 3.08 (s, 3H, >N—C$\underline{H}_3$), 1.50 (d, 3H, J=5.8 Hz, >CH—C$\underline{H}_3$), 1.18 (t, 3H, J=7.2 Hz, >N—CH$_2$-C$\underline{H}_3$).

Mass (m/e): 283 (M+), 198.
Hydrochloride:
M.p. 300° C. (decomp.) (colorless needles) (recrystallized from methanol).
IR$\nu_{max}^{nujol}$ (cm$^{-1}$): 2400–2000, 1680, 1640, 760, 745.

EXAMPLE 50

A mixture of 0.92 g of 1-oxo-2,3-dimethyl-1H-2,3,3a,4,5,6-hexahydro-2,4,10b-triazafluoroanthene (trans isomer), 1.02 g of n-butyl iodide, 0.76 g of anhydrous potassium carbonate and 30 ml of acetonitrile is treated in the same manner as described in Example 48. The crude product thus obtained is purified by silica gel chromatography (Solvent: chloroform). 0.90 g of 1-oxo-2,3-dimethyl-4-n-butyl-1H-2,3,3a,4,5,6-hexahydro-2,4,10b-triazafluoranthene (trans isomer) are thereby obtained as a pale yellow oil. Yield: 80%.

IR$\nu_{max}^{film}$ (cm$^{-1}$): 1690, 1640, 750.

NMR ($\delta$, CDCl$_3$): 8.25 (m, 1H, aromatic), 7.6–7.0 (m, 3H, aromatic), 3.13 (s, 3H,>N—C$\underline{H}_3$), 0.97 (d, 3H, J=6.3 Hz,>CH—C$\underline{H}_3$), 0.95 (t-like, 3H,>N—(CH$_2$)$_3$—C$\underline{H}_3$).

Mass (m/e): 311 (M+), 226 (base peak).
Hydrochloride:
M.p. 233°–235° C. (colorless prisms) (recrystallized from isopropanol).
IR$\nu_{max}^{nujol}$ (cm$^{-1}$): 3570, 3370, 2600–2400, 1690, 1650, 770.

EXAMPLE 51

A mixture of 1.20 g of 1-oxo-2,3-dimethyl-1H, 2,3,3a, 4,5,6-hexahydro-2,4,10b-triazafluoranthene (cis isomer), 1.30 g of n-butyl iodide, 975 mg of anhydrous potassium carbonate and 40 ml of acetonitrile is treated in the same manner as described in Example 48. The crude product thus obtained is purified by silica gel chromatography (Solvent: 0.5% methanol-chloroform). 950 mg of 1-oxo-2,3,-dimethyl-4-n-butyl-1H-2,3,3a,4,5,6-hexahydro-2,4,10b-triazafluoranthene (cis isomer) are thereby obtained.

M.p. 143°–144° C. (colorless needles) (recrystallized from isopropyl ether) Yield: 65.0%.

IR$\nu_{max}^{nujol}$ (cm$^{-1}$): 1690, 1640, 750.

NMR ($\delta$, CDCl$_3$): 8.25 (m, 1H, aromatic), 7.6–7.0 (m, 3H, aromatic), 3.08 (s, 3H, >N—C$\underline{H}_3$), 1.51 (d, 3H, J=5.6Hz, >CH—C$\underline{H}_3$), 0.94 (t-like, 3H, >N—(CH$_2$)$_3$—C$\underline{H}_3$).

Mass (m/e): 311 (M+), 226 (base peak).

Hydrochloride:

M.p. 213°–215° C. (colorless needles) (recrystallized from ethanol).

IR$\nu_{max}^{nujol}$ (cm$^{-1}$): 3540, 3400, 2400–2100, 1680, 1640, 770, 740.

EXAMPLE 52

1-oxo-2-isopropyl-4-benzyl-1H-2,3,3a,4,5,6-hexahydro-2,4,10b-triazafluoranthene is obtained from 1-oxo-2-isopropyl- 1H, 2,3,3a,4,5,6-hexahydro-2,4,10b-triazafluoranthene and benzyl bromide in the same manner as described in Example 25.

M.p. 185°–186° C. (colorless fine needles) (recrystallized from a mixture of ethyl acetate and isopropyl ether).

EXAMPLE 53

1-oxo-2-isopropyl-4-ethyl-1H, 2,3,3a,4,5,6-hexahydro-2,4,10b-triazafluoranthene is obtained from 1-oxo-2-isopropyl-1H-2,3,3a,4,5,6-hexahydro-2,4,10b-triazafluoranthene and ethyl iodide in the same manner as described in Example 25.

Hydrochloride:

M.p. 231°–232° C. (colorless prisms) (recrystallized from ethanol).

EXAMPLE 54

1-oxo-2-n-pentyl-1H,2,3,3a, 4,5,6-hexahydro-2,4,10b-triazafluoranthene is obtained from 1-oxo-2-n-pentyl-1H, 2,3,3a,4,5,6-hexahydro-2,4,10b-triazafluoranthene and benzyl bromide in the same manner as described in Example 25.

M.p. 106°–108° C. (colorless needles) (recrystallized from isopropyl ether).

EXAMPLE 55

1-oxo-2-ethoxycarbonylmethyl-4-benzyl-1H-2,3,3a,4,5,6-hexahydro-2,4,10b-triazafluoranthene is obtained from 1-oxo-2-ethoxycarbonylmethyl-1H-2,3, 3a, 4,5,6-hexahydro-2,4,10b-triazafluoranthene and benzyl bromide in the same manner as described in Example 25.

M.p. 196°–197° C. (colorless fine needles) (recrystallized from ethyl acetate).

EXAMPLE 56

1-oxo-2-(3-methoxycarbonyl-n-propyl)-4-benzyl-1H-2,3,3a,4,5,6-hexahydro-2,4,10b-triazafluoranthene is obtained from 1-oxo-2-(3-methoxycarbonyl-n-propyl)-1H-2,3,3a,4,5,6-hexahydro-2,4,10b-triazafluoranthene and benzyl bromide in the same manner as described in Example 25.

M.p. 126°–131° C. (colorless prisms) (recrystallized from isopropyl ether).

EXAMPLE 57

1-oxo-2-(2-ethoxyethyl)-4-benzyl-1H-2,3,3a,4,5,6-hexahydro-2,4,10b-triazafluoranthene is obtained from 1-oxo-2-(2-ethoxyethyl)-1H-2,3,3a,4,5,6-hexahydro-2,4,10b-triazafluoranthene and benzyl bromide in the same manner as described in Example 25.

Hydrochloride:

M.p. 212°–214° C. (colorless needles) (recrystallized from a mixture of methanol and isopropyl ether).

EXAMPLE 58

1-oxo-2-(2-(tetrahydropyran-2-yl-oxy)ethyl)-4-benzyl-1H-2,3,3a,4,5,6-hexahydro-2,4,10b-triazafluoranthene is obtained from 1-oxo-2-(2-tetrahydropyran-2-yl-oxy)ethyl)-1H-2,3,3a,4,5,6-hexahydro-2,4,10b-triazafluoranthene and benzyl bromide in the same manner as described in Example 25.

M.p. 109°–110° C. (recrystallized from isopropyl ether).

EXAMPLE 59

134 mg of 62% sodium hydride are suspended in 30 ml of anhydrous tetrahydrofuran, and a solution of 1.0 g of 1-oxo-4-benzyl-1H-2,3,3a,4,5,6-hexahydro-2,4,10b-triazafluoranthene in 80 ml of anhydrous tetrahydrofuran is added to the suspension. The mixture is stirred at room temperature for 30 minutes. Then, 0.647 g of benzyl bromide are added to the mixture, and said mixture is further stirred at room temperature for 50 hours. After the reaction, a small amount of methanol is added to the reaction mixture, and said mixture is evaporated under reduced pressure to remove solvent. The residue is dissolved in ethyl acetate, and the solution is washed with water, dried and then evaporated to remove solvent. The residue thus obtained is washed with n-hexane, crystallized with ether and then recrystallized from ethyl acetate. 1.15 g of 1-oxo-2,4-dibenzyl-1H-2,3,3a,4,5,6-hexahydro-2,4,10b-triazafluoranthene are thereby obtained as colorless prisms. Yield: 89.8%.

M.p. 128°–129° C.

IR$\nu_{max}^{nujol}$ (cm$^{-1}$): 1680, 1640, 1595.

NMR ($\delta$, CDCl$_3$): 8.4-8.2 (m, 1H, aromatic), 7.25-7.10 (m, 13H, aromatic), 4.89, 4.55

(d, d, 2H, J = 7.5 Hz, AB type, $-CO\diagdown N-C\underline{H}_2C_6H_5$), 3.6, 3.43 (d, d, 2H, J=7.5 Hz, AB type, N—C$\underline{H}_2$C$_6$H$_5$).

Mass (m/e): 407 (M+).

Hydrochloride:

M.p. 226°–227° C. (decomp.) (pale yellow prisms) (recrystallized from methanol).

IR$\nu_{max}^{nujol}$ (cm$^{-1}$): 2600-2000, 1695, 1650, 1495.

EXAMPLE 60

1.26 g of 66.5% sodium hydride are suspended in 150 ml of anhydrous tetrahydrofuran, and a solution of 10.0 g of 1-oxo-4-benzyl-1H-2,3,3a,4,5,6-hexahydro-2,4,10b-triazafluoranthene in 400 ml of anhydrous tetrahydrofuran is aded to the suspension. The mixture is refluxed for 30 minutes. Then, a solution of 5.36 g of methyl iodide in 30 ml of anhydrous tetrahydrofuran is added dropwise to the mixture, and said mixture is stirred at room temperature for 19 hours. After the reaction mixture is evaporated under reduced pressure, chloroform is added to the residue. The mixture is washed with water, dried and then evaporated to remove solvent. The residue thus obtained is crystallized with ether and then recrystallized from methanol. 9.4 g of 1-oxo-2-methyl-4-benzyl-1H-2,3,3a,4,5,6-hexahydro-2,4,10b-triazafluoranthene are thereby obtained as colorless prisms. Yield: 90.4%

The physico-chemical properties of this product are identical with those of the product obtained in Example 35.

EXAMPLE 61

14.4 g of 1-oxo-4-benzyl-1H-2,3,3a,4,5,6-hexahydro-2,4,10b-triazafluoranthene, 10.6 g of ethyl iodide, 1.98 g of 66% sodium hydride and 600 ml of anhydrous tetrahydrofuran are treated in the same manner as described in Example 60. 13.32 g of 1-oxo-2-ethyl-4-benzyl-1H-2,3,3a,4,5,6-hexahydro-2,4,10b-triazafluoranthene are thereby obtained. Yield: 85.0%.

The physico-chemical properties of this product are identical with those of the product obtained in Example 37.

EXAMPLE 62

0.38 g of 66% sodium hydride are added to a solution of 3.17 g of 1-oxo-4-benzyl-1H-2,3,3a,4,5,6-hexahydro-2,4,10b-triazafluoranthene in 80 ml of dimethylformamide, and the mixture is stirred at room temperature for 30 minutes. 1.48 g of isopropyl bromide are added to the mixture, and said mixture is heated at 50° C. with stirring for 70 hours. After ice-water is added to the reaction mixture, the mixture is extracted with ethyl acetate. The extracts are washed with water, dried and then evaporated to remove solvent. The residue (oil, 2.80 g) is purified by silica gel chromatography (Solvent: chloroform-ethyl acetate (9:1)), and then recrystallized from a mixture of ethyl acetate and isopropyl ether. 2.70 g of 1-oxo-2-isopropyl-4-benzyl-1H-2,3,3a,4,5,6-hexahydro-2,4,10b-triazafluoranthene are thereby obtained as colorless fine needles. Yield: 75.2%.

M.p. 185°–186° C.
IR$\nu_{max}^{nujol}$ (cm$^{-1}$): 1690, 1649.
NMR ($\delta$, CDCl$_3$): 8.23–8.1 (m, 1H, aromatic), 7.5–7.0 (m, 8H, aromatic), 4.81 (m, 1H, >N—C$\underline{H}$(CH$_3$)$_2$), 1.21, 1.09 (d,d, 3H, 3H, J=6.6 Hz, 6.9 Hz, >N—CH(C$\underline{H}_3$)$_2$).
Mass (m/e): 359 (M+).
Hydrochloride:
M.p. 223°–224° C. (colorless fine needles) (recrystallized from ethanol).
IR$\nu_{max}^{nujol}$ (cm$^{-1}$): 2400–1900, 1680, 1650.

EXAMPLE 63

3.17 g of 1-oxo-4-benzyl-1H-2,3,3a,4,5,6-hexahydro-2,4,10b-triazafluoranthene, 2.38 g of n-pentyl iodide, 0.40 g of 66% sodium hydride and 80 ml of anhydrous tetrahydrofuran are treated in the same manner as described in Example 60. 3.4 g of 1-oxo-2-n-pentyl-4-benzyl-1H-2,3,3a,4,5,6-hexahydro-2,4,10b-triazafluoranthene are thereby obtained. Yield: 88.5%.

M.p. 106°–108° C. (colorless prisms) (recrystallized from isopropyl ether).
IR$\nu_{max}^{nujol}$ (cm$^{-1}$): 1688, 1643, 1600.

NMR ($\delta$, CDCl$_3$): 7.32 (s, 5H, —CH$_2$—C$_6$$\underline{H}_5$), 3.50 (s, 2H, —C$\underline{H}_2$—C$_6$H$_5$), 1.94–1.26 (m, 8H), 0.90 (t-like, 3H, —(CH$_2$)$_4$—C$\underline{H}_3$).
Mass (m/e): 387 (M+).
Hydrochloride:
M.p. 208°–211° C. (colorless needles) (recrystallized from ethanol).
IR$\nu_{max}^{nujol}$ (cm$^{-1}$): 2400–1900, 1700(sh), 1685, 1650, 1600.

EXAMPLE 64

3.17 g of 1-oxo-4-benzyl-1H-2,3,3a,4,5,6-hexahydro-2,3,10b-triazafluoranthene, 2.0 g of ethyl bromoacetate, 0.4 g of 66% sodium hydride and 80 ml of dimethylformamide are treated in the same manner as described in Example 62. The crude product thus obtained is purified by silica gel chromatography (Solvent: chloroform-ethyl acetate (5:1)). 3.1 g of 1-oxo-2-ethoxycarbonylmethyl-4-benzyl-1H-2,3,3a,4,5,6-hexahydro-2,4,10b-triazafluoranthene are thereby obtained. Yield: 76.9%

M.p. 196°–197° C. (colorless fine needles) (recrystallized from ethyl acetate).
IR$\nu_{max}^{nujol}$ (cm$^{-1}$): 1735, 1698, 1650.
NMR ($\delta$, CDCl$_3$): 8.30–8.03 (m, 1H, aromatic), 7.50–7.05 (m, 8H, aromatic), 4.22 (s, 2H, —C$\underline{H}_2$—C$_6$H$_5$), 4.15 (q, 2H, J=7 Hz, —C$\underline{H}_2$CH$_3$), 1.21 (t, 3H, J=7 Hz, —CH$_2$C$\underline{H}_3$).
Mass (m/e): 403 (M+).
Hydrochloride:
M.p. 207°–208° C. (decomp.) (colorless needles) (recrystallized from ethanol).
IR$\nu_{max}^{nujol}$ (cm$^{-1}$): 2500–2100, 1740, 1700, 1650.

EXAMPLE 65

105 mg of potassium hydroxide are added to a solution of 1.0 g of 1-oxo-4-benzyl-1H-2,3,3a,4,5,6-hexahydro-2,4,10b-triazafluoranthene in 30 ml of dimethylsulfoxide. The mixture is stirred at room temperature for 30 minutes, and 652 mg of methyl 4-bromobutylate are added dropwise thereto. The mixture is stirred at room temperature for 20 hours, and then heated at 50° C. with stirring for 72 hours. After the reaction mixture is poured into water, the aqueous mixture is extracted with ethyl acetate. The extracts are washed with water, dried and then evaporated to remove solvent. The residue (1.0 g) is purified by silica gel chromatography (Solvent: chloroform-ethyl acetate (4:1)). 0.37 g of 1-oxo-2-(3-methoxycarbonylpropyl)-4-benzyl-1H-2,3,3a,4,5,6-hexahydro-2,4,10b-triazafluoranthene are thereby obtained. Yield: 29.6%.

M.p. 126°–131° C. (colorless prisms) (recrystallized from isopropyl ether).
IR$\nu_{max}^{nujol}$ (cm$^{-1}$): 1760, 1730, 1690, 1650.
NMR ($\delta$,CDCl$_3$): 8.35–8.10 (m, 1H, aromatic), 7.50–7.10 (m, 8H, aromatic), 3.65 (s, 3H, —COOC$\underline{H}_3$), 3.56 (s, 2H, —C$\underline{H}_2$C$_6$H$_5$).
Mass (m/e): 417 (M+).

EXAMPLE 66

1.85 g of 1-oxo-4-benzyl-1H-2,3,3a,4,5,6-hexahydro-2,4,10b-triazafluoranthene, 1.07 g of 2-ethoxyethyl bromide, 0.23 g of 66% sodium hydride and 45 ml of dimethylformamide are treated in the same manner as described in Example 62. The crude product is purified by silica gel chromatography (Solvent: chloroform-ethyl acetate (4:1)). 1.9 g of 1-oxo-2-(2-ethoxyethyl)-4-benzyl- 1H-2,3,3a,4,5,6-hexahydro-2,4,10b-triazafluoranthene are thereby obtained as an oil. Yield: 84.0%.

IR$\nu_{max}^{film}$ (cm$^{-1}$): 1700 (sh), 1690, 1645.

NMR ($\delta$, CDCl$_3$): 8,25 (m,1H, aromatic), 7.5–7.1 (m, 8H, aromatic) 3.65 (q, 2H, J=7.5 Hz, >N—CH$_2$C-H$_2$OCH$_2$CH$_3$), 1.20 (t, 3H, J=7.5 Hz, >N—CH$_2$C-H$_2$OCH$_2$ CH$_3$).

Mass (m/e): 389 (M+).

Hydrochloride:

M.p. 212°–214° C. (colorless needles) (recrystallized from a mixture of methanol and isopropyl ether).

IR$\nu_{max}^{nujol}$ (cm$^{-1}$): 2600–2000, 1700, 1645.

EXAMPLE 67

(1) 3.17 g of 1-oxo-4-benzyl-1H-2,3,3a,4,5,6-hexahydro-2,4,10b-triazafluoranthene, 2.5 g of 2-(tetrahydropyran-2-yl-oxy)ethyl bromide, 0.40 g of 66% sodium hydride and 80 ml of dimethylformamide are treated in the same manner as described in Example 62. The crude product thus obtained is purified by silica gel chromatography (Solvent: chloroform-ethyl acetate (3:1)). 3.91 g of 1-oxo-2-(2-(tetrahydropyran-2-yl-oxy)ethyl)-4-benzyl-1H-2,3,3a,4,5,6-hexahydro-2,4,10b-triazafluoranthene are thereby obtained. Yield: 90%.

M.p. 109°–110° C. (recrystallized from isopropyl ether).

IR$\nu_{max}^{nujol}$ (cm$^{-1}$): 1690, 1645, 1600.

NMR ($\delta$, CDCl$_3$): 8.25–8.10 (m, 1H, aromatic), 7.5–7.10 (m, 3H, aromatic), 7.34 (s, 5H, aromatic), 4.61 (broad s, 1H), 2.67 (s, 2H), 1.8–1.3 (m, 6H).

Mass (m/e): 445 (M+).

(2) 10 ml of ethanol, 10 ml of water and 1 ml of conc. hydrochloric acid are added to 350 mg of 1-oxo-2-(2-(tetrahydropyran-2-yl-oxy)ethyl)-4-benzyl-1H-2,3,3a,4,5,6-hexahydro-2,4,10b-triazafluoranthene, and the mixture is stirred at room temperature for 24 hours. After the reaction mixture is condensed, water is added to the residue. Potassium carbonate is added to the aqueous mixture under ice-cooling, and said mixture is extracted with ethyl acetate. The extracts are washed with water, dried and then evaporated to remove solvent. 0.27 g of 1-oxo-2-(2-hydroxyethyl)-4-benzyl-1H-2,3,3a,4,5,6-hexahydro-2,4,10b-triazafluoranthene are thereby obtained. Yield: 95.0%.

M.p. 154°–159° C. (colorless needles) (recrystallized from ethyl acetate).

IR$\nu_{max}^{nujol}$ (cm$^{-1}$): 3475, 1672, 1643, 1600, 1480.

NMR ($\delta$, CDCl$_3$): 8.35–8.10 (m, 1H, aromatic), 7.55–7.10 (m, 8H, aromatic), 3.76 (m, 2H, CH$_2$CH$_2$OH), 3.69 (t, 2H, NCH$_2$CH$_2$), 3.60 (s, 2H, CH$_2$C$_6$H$_5$), 2.85 (m, 1H, OH).

Hydrochloride:

M.p. 218°–222° C. (decomp.) (colorless prisms) (recrystallized from methanol).

IR$\nu_{max}^{nujol}$ (cm$^{-1}$): 3340, 2380, 2200, 1690, 1680, 1650.

EXAMPLE 68

A mixture of one g of 1-oxo-4-ethyl-1H-2,3,3a,4,5,6-hexahydro-2,4,10b-triazafluoranthene, 0.802 g of benzyl bromide, 0.156 g of 66% sodium hydride and 30 ml of tetrahydrofuran is treated in the same manner as described in Example 60. 1.13 g of 1-oxo-2-benzyl-4-ethyl-1H-2,3,3a,4,5,6-hexahydro-2,4,10b-triazafluoranthene are thereby obtained. Yield: 83.7%.

M.p. 126°–128° C. (colorless prisms) (recrystallized from ethanol).

IR$\nu_{max}^{nujol}$ (cm$^{-1}$): 1695, 1650, 1600.

NMR ($\delta$, CDCl$_3$): 7.35 (s, 5H, —CH$_2$C$_6$H$_5$), 4.75 (2H, —CH$_2$C$_6$H$_5$).

Mass (m/e): 345 (M+).

Hydrochloride:

M.p. 228° C. (decomp.) (colorless scales) (recrystallized from ethanol).

IR$\nu_{max}^{nujol}$ (cm$^{-1}$): 2600–2000, 1700, 1645.

EXAMPLE 69

A mixture of 1.04 g of 1-oxo-4-ethyl-1H-2,3,3a,4,5,6-hexahydro-2,4,10b-triazafluoranthene, 0.636 g of 3-(dimethylamino)propyl chloride, 0.161 g of 66% sodium hydride and 30 ml of dimethylformamide is treated in the same manner as described in Example 62. 1.24 g of 1-oxo-2-(3-(dimethylamino) propyl)-4-ethyl-1H-2,3,3a,4,5,6-hexahydro-2,4,10b-triazafluoranthene are thereby obtained as an oil. Yield: 90.5%.

IR$\nu_{max}^{film}$ (cm$^{-1}$): 1695, 1645.

NMR ($\delta$, CDCl$_3$): 8.30–8.15 (m, 1H, aromatic), 7.60–7.10 (m, 3H, aromatic), 2.30 (s, 6H, >N(CH$_3$)$_2$, 1.20 (t, 3H, J=7 Hz, —CH$_2$CH$_3$).

Mass (m/e): 340 (M+).

Hydrochloride:

M.p. 232°–233° C. (pale yellow powder) (recrystallized from ethanol).

IR$\nu_{max}^{nujol}$ (cm$^{-1}$): 2600–2000, 1700, 1645.

EXAMPLE 70

A mixture of 0.7 g of 1-oxo-4-ethyl-1H-2,3,3a,4,5,6-hexahydro-2,4,10b-triazafluoranthene, 0.46 g of methyl iodide, 0.11 g of 66.5% sodium hydride and 35 ml of anhydrous tetrahydrofuran is treated in the same manner as described in Example 60. The crude product thus obtained is purified by silica gel chromatography (Solvent: chloroformethyl acetate (2:1)). 0.71 g of 1-oxo-2-methyl-4-ethyl-1H-2,3,3a,4,5,6-hexahydro-2,4,10b-triazafluoranthene are thereby obtained as an oil. Yield: 96%.

The physico-chemical properties of this product are identical with those of the product obtained in Example 26.

EXAMPLE 71

A mixture of 1.30 g of 1-oxo-4-ethyl-1H-2,3,3a,4,5,6-hexahydro-2,4,10b-triazafluoranthene, 936 mg of ethyl iodide, 220 mg of 66% sodium hydride and 30 ml of anhydrous tetrahydrofuran is treated in the same manner as described in Example 70. 0.75 g of 1-oxo-2,4-diethyl-1H-2,3,3a,4,5,6-hexahydro-2,4,10b-triazafluoranthene are thereby obtained. Yield: 53.2%.

The physico-chemical properties of this product are identical with those of the product obtained in Example 39.

EXAMPLE 72

A mixture of one g of 1-oxo-4-ethyl-1H-2,3,3a,4,5,6-hexahydro-2,4,10b-triazafluoranthene, 0.577 g of isopropyl bromide, 0.156 g of 66.5% sodium hydride and 30 ml of anhydrous tetrahydrofuran is treated in the same manner as described in Example 70. 0.73 g of 1-oxo-2-isopropyl-4-ethyl-1H-2,3,3a,4,5,6-hexahydro-2,4,10b-triazafluoranthene are thereby obtained as an oil. Yield: 63%.

IR$\nu_{max}^{film}$ (cm$^{-1}$): 1690, 1650.

NMR ($\delta$, CDCl$_3$): 4.85 (m, 1H, —CH(CH$_3$)$_2$), 1.28, 1.17 (d,d 3H×2, J=7 Hz, J=7 Hz, —CH$_3$)$_2$).

Mass (m/e): 297 (M+).

Hydrochloride:

EXAMPLE 73

A mixture of 1.0 g of 1-oxo-4-n-butyl-1H-2,3,3a,4,5,6-hexahydro-2,4,10b-triazafluoranthene, 0.752 g of methyl iodide, 0.857 g of anhydrous potassium carbonate and 10 ml of dimethylformamide is stirred at room temperature for 5 days. After the reaction, the reaction mixture is poured into ice-water, and the aqueous mixture is extracted with ethyl acetate. The extract is washed with water, dried and then evaporated to remove solvent. The residue is recrystallized from a mixture of isopropyl ether and n-hexane. One g of 1-oxo-2-methyl-4-n-butyl-1H-2,3,3a,4,5,6-hexahydro-2,4,10b-triazafluoranthene is thereby obtained as colorless scales. Yield: 83.3%.

The physico-chemical properties of this product are identical with those of the product obtained in Example 29.

EXAMPLE 74

A mixture of 1.4 g of 1-oxo-4-n-butyl-1H-2,3,3a,4,5,6-hexahydro-2,4,10b-triazafluoranthene, 1.01 g of ethyl iodide, 1.04 g of anhydrous potassium carbonate and 18 ml of dimethylformamide is treated in the same manner as described in Example 73. The crude product thus obtained is purified by silica gel chromatography (Solvent: ethyl acetate-chloroform (1:4)). 1.2 g of 1-oxo-2-ethyl-4-n-butyl-1H-2,3,3a,4,5,6-hexahydro-2,4,10b-triazafluoranthene are thereby obtained as an oil. Yield: 76.9%.

The physico-chemical properties of this product are identical with those of the product obtained in Example 41.

EXAMPLE 75

A mixture of 1.4 g of 1-oxo-4-n-butyl-1H-2,3,3a,4,5,6-hexahydro-2,4,10b-triazafluoranthene, 1.26 g of n-pentyl iodide, 1.04 g of anhydrous potassium carbonate and 18 ml of dimethylformamide is treated in the same manner as described in Example 74. 1.32 g of 1-oxo-2-n-pentyl-4-n-butyl-1H-2,3,3a,4,5,6-hexahydro-2,4,10b-triazafluoranthene are thereby obtained as an oil. Yield: 75.0%.

The physico-chemical properties of this product are identical with those of the product obtained in Example 44.

EXAMPLE 76

A mixture of 0.595 mg of 1-oxo-4-n-butyl-1H-2,3,3a,4,5,6-hexahydro-2,4,10b-triazafluoranthene, 453 mg of methyl 4-bromobutylate, 84 mg of 66% sodium hydride and 15 ml of dimethylsulfoxide is treated in the same manner as described in Example 62. 220 mg of 1-oxo-2-(3-methoxycarbonyl-n-propyl)-4-n-butyl-1H-2,3,3a,4,5,6-hexahydro-2,4,10b-triazafluoranthene are thereby obtained. Yield: 27.2%.

IR$\nu_{max}^{liquid}$ (cm$^{-1}$): 1740, 1690, 1643.

NMR ($\delta$, CDCl$_3$): 8.30–8.10 (m, 1H, aromatic), 7.50–7.05 (m, 3H, aromatic), 3.65 (s, 3H, —COOCH$_3$), 1.60–1.10 (m, 6H), 1.05–0.80 (m, 3H, —(CH$_2$)$_3$CH$_3$).

Mass (m/e): 383 (M$^+$).

Hydrochloride:

M.p. 181°–183° C. (colorless prisms) (recrystallized from a mixture of methanol and isopropyl ether).

IR$\nu_{max}^{nujol}$ (cm$^{-1}$): 2600–2200, 1735, 1710, 1650.

M.p. 231°–232° C. (colorless prisms) (recrystallized from ethanol).

IR$\nu_{max}^{nujol}$ (cm$^{-1}$): 2500–2000, 1697, 1645.

EXAMPLE 77

A mixture of 4.43 g of 1-oxo-3-methyl-4-benzyl-1H-2,3,3a,4,5,6-hexahydro-2,4,10b-triazafluoranthene (trans isomer), 2.35 g of methyl iodide, 600 mg of 60% sodium hydride and 210 ml of anhydrous tetrahydrofuran is treated in the same manner as described in Example 60. 4.51 g of 1-oxo-2,3-dimethyl-4-benzyl-1H-2,3,3a,4,5,6-hexahydro-2,4,10b-triazafluoranthene (trans isomer) are thereby obtained as colorless prisms. Yield: 97.5%.

M.p. 152°–153° C.

IR$\nu_{max}^{nujol}$ (cm$^{-1}$): 1690, 1640, 780, 770, 750, 710.

NMR ($\delta$, CDCl$_3$): 8.25 (m, 1H, aromatic), 7.6–7.0 (m, 8H, aromatic), 4.2–2.2 (m, 8H), 3.15 (s, 3H, >N—CH$_3$), 1.10 (d, 3H, J=6.2 Hz, >CHCH$_3$).

Mass (m/e): 345 (M$^+$), 260 (base peak).

Hydrochloride:

M.p. 211°–213° C. (decomp.) (colorless needles) (recrystallized from ethyl acetate).

IR$\nu_{max}^{nujol}$ (cm$^{-1}$): 3300, 3200, 2700–2300, 1710, 1640, 760, 740, 700.

EXAMPLE 78

A mixture of 4.66 g of 1-oxo-3-methyl-4-benzyl-1H-2,3,3a,4,5,6-hexahydro-2,4,10b-triazafluoranthene (cis isomer), 2.42 g of methyl iodide, 620 mg of 60% sodium hydride and 210 ml of anhydrous tetrahydrofuran is treated in the same manner as described in Example 60. 4.76 g of 1-oxo-2,3-dimethyl-4-benzyl-1H-2,3,3a,4,5,6-hexahydro-2,4,10b-triazafluoranthene (cis isomer) are thereby obtained.

M.p. 162°–163° C. (colorless needles) (recrystallized from ethyl acetate).

IR$\nu_{max}^{nujol}$ (cm$^{-1}$): 1685, 1625, 760, 755, 745, 700.

NMR ($\delta$, CDCl$_3$): 8.3 (m, 1H, aromatic), 7.6–7.0 (m, 8H, aromatic), 4.2–2.4 (m, 8H), 3.06 (s, 3H, >N—CH$_3$), 1.47 (d, 3H, J=5.6 Hz, >CHCH$_3$).

Mass (m/e): 345 (M$^+$), 260 (base peak).

Hydrochloride:

M.p. 281°–283° C. (decomp.) (colorless needles) (recrystallized from a mixture of ethyl acetate and methanol).

IR$\nu_{max}^{nujol}$ (cm$^{-1}$): 2400–2200, 1695, 1640, 770, 750, 710.

EXAMPLE 79

1-oxo-2-isopropyl-4-n-butyl-1H-2,3,3a,4,5,6-hexahydro-2,4,10b-triazafluoranthene is obtained from 1-oxo-4-n-butyl-1H-2,3,3a,4,5,6-hexahydro-2,4,10b-triazafluoranthene and isopropyl iodide in the same manner as described in Example 62.

The physico-chemical properties of this product are identical with those of the product obtained in Example 43.

EXAMPLE 80

1-oxo-2-ethoxycarbonylmethyl-4-n-butyl-1H-2,3,3a,4,5,6-hexahydro-2,4,10b-triazafluoranthene is obtained from 1-oxo-4-n-butyl-1H-2,3,3a,4,5,6-hexahydro-2,4,10b-triazafluoranthene and ethyl bromoacetate in the same manner as described in Example 62.

The physico-chemical properties of this product are identical with those of the product obtained in Example 45.

EXAMPLE 81

1-oxo-2-(2-ethoxyethyl)-4-n-butyl-1H-2,3,3a,4,5,6-hexahydro-2,4,10b-triazafluoranthene is obtained from 1-oxo-4-n-butyl-1H-2,3,3a,4,5,6-hexahydro-2,4,10b-triazafluoranthene and 2-ethoxyethyl bromide in the same manner as described in Example 62.

The physico-chemical properties of this product are identical with those of the product obtained in Example 46.

EXAMPLE 82

(1) 1-oxo-2-(2-(tetrahydropyran-2-yl-oxy)ethyl)-4-n-butyl-1H-2,3, 3a,4,5,6-hexahydro-2,4,10b-triazafluoranthene is obtained from 1-oxo-4-n-butyl-1H-2,3,3a,4,5,6-hexahydro-2,4,10b-triazafluoranthene and 2-(tetrahydropyran-2-yl-oxy)ethylbromide in the same manner as described in Example 62.

(2) 1-oxo-2-(2-tetrahydropyran-2-yl-oxy)ethyl)-4-n-butyl-1H-2,3,3a,4,5,6-hexahydro-2,4,10b-triazafluoranthene is treated in the same manner as described in Example 47, whereby 1-oxo-2-(2-hydroxyethyl)-4-n-butyl-1H-2,3,3a,4,5,6-hexahydro-2,4,10b-triazafluoranthene is obtained.

The physico-chemical properties of this product are identical with those of the product obtained in the Example 47.

EXAMPLE 83

A mixture of 1.04 g of 1-oxo-2-methyl-1H-2,3,3a,4,5,6-hexahydro-2,4,10b-triazafluoranthene, 10 ml of methyl acrylate and 0.1 ml of acetic acid is heated at 50° C. with stirring for 4 hours. After the reaction, 20 ml of 10% hydrochloric acid and 200 ml of water are added to the reaction mixture under ice-cooling, and the mixture is extracted with ether. The aqueous layer is alkalized with potassium carbonate under cooling, and then extracted with ethyl acetate. The extracts are washed with water, dried and then evaporated to remove solvent. The residue (oil, 1.6 g) is purified by alumina chromatography (Solvent: benzene-ethyl acetate(1:1)). 1.0 g of 1-oxo-2-methyl-4-(2-methoxycarbonylethyl)-1H-2,3,3a,4,5,6-hexahydro-2,4,10b-triazafluoranthene is thereby obtained. Yield: 74.6%.

M.p. 128°–130° C. (colorless prisms) (recrystallized from ether).

IR$\nu_{max}^{nujol}$ (cm$^{-1}$): 1735, 1690, 1640, 1480.

NMR (δ, CDCl$_3$): 8.25–8.10 (m, 1H, aromatic), 7.35–7.10 (m, 3H, aromatic), 3.70 (s, 3H, —COOCH$_3$), 3.18 (s, 3H, >N—CH$_3$).

Mass (m/e): 327 (M+).
Hydrochloride:

M.p. 203°–221° C. (decomp.) (pale yellow fine needles) (recrystallized from a mixture of methanol and isopropyl ether).

EXAMPLE 84

A mixture of 1.0 g of 1-oxo-2-methyl-1H-2,3,3a,4,5,6-hexahydro-2,4,10b-triazafluoranthene, 5 ml of methyl vinyl ketone and 0.1 ml of acetic acid is treated in the same manner as described in Example 83. The crude product (oil, 1.3 g) thus obtained is crystallized with ether, whereby 1.10 g of 1-oxo-2-methyl-4-(2-acetylethyl)-1H-2,3,3a,4,5,6-hexahydro-2,4,10b-triazafluoranthene are obtained. Yield: 85.9%.

M.p. 128°–129° C. (colorless scales) (recrystallized from ethyl acetate).

IR$\nu_{max}^{nujol}$ (cm$^{-1}$): 1705, 1690, 1650, 1480.

NMR (δ, CDCl$_3$): 3.13 (s, 3H, >N—CH$_3$), 2.15 (s, 3H, —COCH$_3$).

Mass (m/e): 311 (M+).
Hydrochloride:

M.p. 198°–239° C. (decomp.) (yellow needles) (recrystallized from a mixture of methanol and isopropyl ether).

IR$\nu_{max}^{nujol}$ (cm$^{-1}$): 2600–2000, 1710, 1650, 1495.

EXAMPLE 85

A mixture of 1.30 g of 1-oxo-2-ethyl-1H-2,3,3a,4,5,6-hexahydro-2,4,10b-triazafluoranthene, 5 ml of methyl vinyl ketone and a drop of acetic acid is treated in the same manner as described in Example 83. The crude product thus obtained is converted into its hydrochloride by using a mixture of isopropyl ether and ethanolic hydrogen chloride, whereby 1.26 g of 1-oxo-2-ethyl-4-(2-acetylethyl)-1H-2,3,3a,4,5,6-hexahydro-2,4,10b-triazafluoranthene hydrochloride are obtained. Yield: 69.6%.

M.p. 253° C. (decomp.) (colorless prisms) (recrystallized from ethanol).

IR$\nu_{max}^{nujol}$ (cm$^{-1}$): 1700, 1690, 1650.

NMR (δ, CDCl$_3$): 2.19 (s, 3H, —COCH$_3$), 1.23 (t, 3H, >N—CH$_2$CH$_3$).

Mass (m/e): 325 (M+).

EXAMPLE 86

A mixture of 0.85 g of 1-oxo-2-(3-methoxycarbonyl-n-propyl)-4-n-butyl-1H-2,3,3a,4,5,6-hexahydro-2,4,10b-triaza fluoranthene, 10 ml of ethanol and 10 ml of an aqueous 10% sodium hydroxide solution is stirred at room temperature for 20 hours. After the reaction, the reaction mixture is condensed to remove ethanol. 10 ml of water are added to the residue, and the aqueous mixture is adjusted to pH 7 with acetic acid. The resultant precipitate is extracted with ethyl acetate. The extracts are washed with water, dried and then evaporated to remove solvent. The residue thus obtained is recrystallized from methanol. 0.46 g of 1-oxo-2-(3-carboxy-n-propyl)-4-n-butyl-1H-2,3,3a,4,5,6-hexahydro-2,4,10b-triazafluoranthene are thereby obtained as colorless prisms. Yield: 56.8%.

M.p. 180°–183° C.

IR$\nu_{max}^{nujol}$ (cm$^{-1}$): 2100–1850, 1690, 1642.

NMR (δ, CDCl$_3$+DMSO-d$_6$): 8.50 (broad s, 1H, —COOH), 8.30–8.05 (m, 1H, aromatic), 7.50–7.05 (m, 3H, aromatic), 1.6–1.10 (m, 6H), 1.10–0.7 (m, (3H, —(CH$_2$)$_3$CH$_3$)).

Mass (m/e): 369 (M+).
Hydrochloride:

M.p. 216°–217° C. (decomp.) (colorless powder).

IR$\nu_{max}^{nujol}$ (cm$^{-1}$): 3050, 2700–2300, 1730, 1692, 1650.

EXAMPLE 87

To a solution of 200 mg of 1-oxo-2,3-dimethyl-1H-2,3,3a,4,5,6-hexahydro-2,4,10b-triazafluoranthene (trans isomer) in 3 ml of pyridine, 1.5 ml of acetic anhydride are added dropwise under ice-cooling. The mixture is stirred at room temperature for 1.5 hours. After the reaction, ice is added to the reaction mixture, and said mixture is extracted with ethyl acetate. The extracts are washed with water, dil. hydrochloric acid and a saturated sodium chloride solution, dried and then evaporated to remove solvent. The residue is recrystallized from a mixture of n-hexane and benzene. 206 mg of 1-oxo-2,3-dimethyl-4-acetyl-1H-2,3,3a,4,5,6-hexahydro-2,4,10b-triazafluoranthene (trans isomer) are thereby obtained as colorless prisms. Yield: 88.5%.

M.p. 141°–143° C.

IR$\nu_{max}^{nujol}$ (cm$^{-1}$): 1690, 1640, 775, 760, 775, 740, 710.

NMR (δ, CDCl$_3$): 8.30 (m, 1H, aromatic), 7.6-7.0 (m, 6H, aromatic), 5.48 (d, 1H, J=5.0 Hz, C$_{3a}$-H), 3.13 (s, 3H, >N—CH$_3$), 2.25 (s, 3H, COCH$_3$), 0.93 (d, 3H, J=6.7 Hz, CH—CH$_3$).

Mass (m/e): 297 (M+), 225, 170 (base peak).

Analysis calculated for C$_{17}$H$_{19}$N$_3$O$_2$·½C$_6$H$_6$ C, 71,41; H, 6.59; N, 12.49.

Found: C, 71.48; H, 6.74; N, 12.44.

EXAMPLE 88

A mixture of 300 mg of 1-oxo-2,3-dimethyl-1H-2,3,3a,4,5,6-hexahydro-2,4,10b-triazafluoranthene (cis isomer), 2 ml of acetic anhydride and 5 ml of pyridine is treated in the same manner as described in Example 87. 325 mg of 1-oxo-2,3-dimethyl-4-acetyl-1H-2,3,3a,4,5,6-hexahydro-2,4,10b-triazafluoranthene (cis isomer) are thereby obtained.

M.p. 177°-178° C. (colorless needles) (recrystallized from a mixture of isopropyl ether and benzene).

NMR (δ, CDCl$_3$): 8.25 (m, 1H, aromatic), 7.6-7.0 (m, 3H, aromatic), 5.56 (d, 1H, J=11.1 Hz, C$_{3a}$-H), 3.08 (s, 3H, >N—CH$_3$), 1.40 (d, 3H, J=6.6 Hz, >CH—CH$_3$).

Mass (m/e): 297 (M+), 225, 170 (base peak).

EXAMPLE 89

(1) To a solution of 3.4 g of N-n-butyl-tryptamine in 50 ml of toluene are added 4.6 g of N-methyl-N-benzyloxycarbonyl-2-aminopropionaldehyde, and the mixture is refluxed for 15 hours. After the reaction, the mixture is condensed under reduced pressure. Then, the residue obtained is purified by silica gel chromatography. 3.9 g of 1,2,3,4-tetrahydro-1-(2-N-methyl-N-benzyloxycarbonylamino)ethyl)-2-n-butyl-β-carboline (cis isomer) and 1.32 g of 1,2,3,4-tetrahydro-1-(2-(N-methyl-N-benzyloxycarbonylamino)ethyl-2-n-butyl-β-carboline (trans isomer) are obtained, respectively.

cis isomer: M.p. 120°-123° C.

IR$\nu_{max}^{nujol}$ (cm$^{-1}$): 3380, 1685.

NMR (δ, CDCl$_3$): 1.45 (3H, d, >CH—CH$_3$, J=6 Hz), 2.90 (3H, s, NCH$_3$).

Mass (m/e): 419 (M+).

trans isomer: pale yellow oil

IR$\nu_{max}^{liq.}$ (cm$^{-1}$): 3320, 1690, 1675.

NMR (δ, CDCl$_3$): 1.30 (3H, d, >CH—CH$_3$, J=6 Hz), 3.09 (3H, s, NCH$_3$).

Mass (m/e): 419 (M+).

(2) To a solution of 1,2,3,4-tetrahydro-1-(2-(N-methyl-N-benzyloxycarbonylamino)-2-n-butyl-β-carboline (cis isomer) in 40 ml of benzene are added 250 mg of 60% sodium hydride, and the mixture is stirred for 30 minutes under heating at 100° C. The reaction mixture is condensed to dryness. After cooling, water is added to the residue, and the aqueous mixture is extracted with chloroform. The extracts are washed with water, dried and condensed to dryness. The residue thus obtained is purified by silica gel chromatography. 605 mg of 1-oxo-2,3-dimethyl-4-n-butyl-1H-2,3,3a,4,5,6-hexahydro-2,4,10b-triazafluoranthene (cis isomer) are thereby obtained. The physiochemical properties of this product are identical with those of the sample obtained in Example 51.

(3) A mixture of 157 mg of 60% sodium hydride and a solution of 660 mg of 1,2,3,4-tetrahydro-1-(2-(N-methyl-N-benzyloxycarbonylamino)ethyl)-2-n-butyl-β-carboline (trans isomer) in benzene is treated in the same manner as described in paragraph (2). 355 mg of 1-oxo-2,3-dimethyl-4-n-butyl-1H-2,3,3a,4,5,6-hexahydro-2,4,10b-triazafluoranthene (trans isomer) are obtained. The physico-chemical properties of this product are identical with those of the sample obtained in Example 50.

What we claim is:

1. A triazafluoranthene compound of the formula:

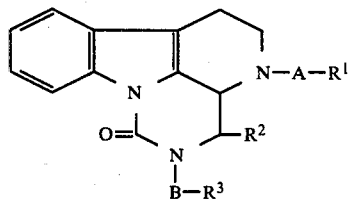

wherein R$^1$ is hydrogen, phenyl or cycloalkyl of 3 to 6 carbon atoms, R$^2$ is hydrogen or lower alkyl, R$^3$ is hydrogen, lower alkoxy or (lower alkoxy)carbonyl, A is single bond, alkylene of one to five carbon atoms or alkenylene of 2 to 5 carbon atoms and B is single bond or alkylene of one to five carbon atoms, or a pharmaceutically acceptable acid addition salt thereof.

2. The compound of claim 1, in which R$^1$ is hydrogen, phenyl or cyclohexyl, R$^2$ is hydrogen or methyl, R$^3$ is hydrogen, ethoxy or ethoxycarbonyl, A is single bond, 3-methyl-2-n-butenylene or alkylene of one to five carbon atoms and B is single bond or alkylene of one to five carbon atoms.

3. The compound of claim 2, in which R$^1$, R$^2$ and R$^3$ are hydrogen, A is alkylene of two to five carbon atoms and B is single bond or methylene.

4. The compound of claim 3 in which R$^1$, R$^2$ and R$^3$ are hydrogen, A is alkylene of two to five carbon atoms and B is methylene.

5. The compound of claim 3, in which R$^1$, R$^2$ and R$^3$ are hydrogen, A is alkylene of two to four carbon atoms and B is methylene.

6. The compound of claim 4, in which R$^1$, R$^2$ and R$^3$ are hydrogen, A is alkylene of four carbon atoms and B is methylene.

7. The compound of claim 2 which is 1-oxo-2,3-dimethyl-4-n-butyl-1H-2,3,3a,4,5,6-hexahydro-2,4,10b-triazafluoranthene or a pharmaceutically acceptable acid addition salt thereof.

8. The compound of claim 2 which is 1-oxo-2-ethyl-4-n-pentyl-1H-2,3,3a,4,5,6-hexahydro-2,4,10b-triazafluoranthene or a pharmaceutically acceptable acid addition salt thereof.

9. The compound of claim 2 which is 1-oxo-2-methyl-4-cyclohexylmethyl-1H-2,3,3a,4,5,6-hexahydro-2,4,10b-triazafluoranthene or a pharmaceutically acceptable acid addition salt thereof.

10. The compound of claim 2 which is 1-oxo-2,3-dimethyl-4-benzyl-1H-2,3,3a,4,5,6-hexahydro-2,4,10b-triazafluoranthene or a pharmaceutically acceptable acid addition salt thereof.

11. The compound of claim 3 which is 1-oxo-2methyl-4-ethyl-1H-2,3,3a,4,5,6-hexahydro-2,4,10b-triazafluoranthene or a pharmaceutically acceptable acid addition salt thereof.

12. The compound of claim 3 which is 1-oxo-2-methyl-4-n-propyl-1H-2,3,3a,4,5,6-hexahydro-2,4,10b-triazafluoranthene or a pharmaceutically acceptable acid addition salt thereof.

13. The compound of claim 3 which is 1-oxo-2-methyl-4-n-butyl-1H-2,3,3a,4,5,6-hexahydro-2,4,10b-triaza-fluoranthene or a pharmaceutically acceptable acid addition salt thereof.

14. The compound of claim 3 which is 1-oxo-2-methyl-4-n-pentyl-1H-2,3,3a,4,5,6-hexahydro-2,4,10b-triaza-fluoranthene or a pharmaceutically acceptable acid addition salt thereof.

15. A pharmaceutical composition which comprises a therapeutically effective amount of a compound of the formula:

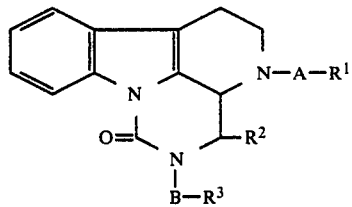

wherein $R^1$ is hydrogen, phenyl or cycloalkyl of 3 to 6 carbon atoms, $R^2$ is hydrogen or lower alkyl, $R^3$ is hydrogen, lower alkoxy or (lower alkoxy)carbonyl, A is single bond, alkylene of one to five carbon atoms or alkenylene of 2 to 5 carbon atoms and B is single bond or alkylene of one to five carbon atoms, or a pharmaceutically acceptable acid addition salt thereof, and a pharmaceutically acceptable carrier therefor.

* * * * *

UNITED STATES PATENT AND TRADEMARK OFFICE
CERTIFICATE OF CORRECTION

PATENT NO. : 4,367,230
DATED : January 4, 1983
INVENTOR(S) : SATO, et al

It is certified that error appears in the above-identified patent and that said Letters Patent are hereby corrected as shown below:

Column 7, line 55, change "1H, 2" to --1H-2--
Column 8, line 11, correct "formamide"
Column 9, line 14, after "$R^3{}'$," insert --$R^4$,--
Column 9, line 24, correct "dimethylforma-"
Column 9, lines 45-46, change "23", "29", and "43" to --$\underline{23}$--, --$\underline{29}$-- and --$\underline{43}$-- respectively
Column 9, line 66, correct "dicyclohexylcarbodiimide"
Column 10, line 9, correct "dimethylformamide"
Column 10, line 52, after "(1978)" insert --)--and correct "1-oxo-2-methyl-4-n-pentyl-"
Column 11, line 20, after "or" insert --may--
Column 12, line 35, correct "activity"
Column 13, line 36, correct "1H-2,3,3a,4,5,6-"
Column 14, line 19, change "2700-1710" to --2700-2200, 1710--
Column 14, line 27, change "ethanol" to --methanol--
Column 15, line 36, correct "tryptamine"
Column 15, line 44, change "(1:1)" to --(1:1))--
Column 17, line 28, change "62" to --$\beta$--
Column 17, line 35, change "0.165" to --0.615--
Column 17, line 38, correct "-25°C"
Column 19, line 63, column 22, line 29, and column 32, line 40, Correct "($M^+$)"
Column 26, line 67, correct "chloroform-ethyl"
Column 28, line 42, correct "(s,3H, >N-C$\underline{H}_3$)"
Column 29, line 13, correct "acetate-chloroform"
Column 29, lines 23-24, correct "chloroform-methanol"
Column 29, line 59, correct "methanol-chloroform"
Column 30, line 66, correct "1.10-0.78"-
Column 31, line 19, correct "(t, 3H, J=7.5Hz, -OCH$_2$-C$\underline{H}_3$)"

Column 33, line 38, and line 50, change "1H, 2, 3" to --1H-2,3--

UNITED STATES PATENT AND TRADEMARK OFFICE
CERTIFICATE OF CORRECTION

PATENT NO. : 4,367,230                              Page 2 of 2

DATED     : January 4, 1983

INVENTOR(S) : SATO, et al

It is certified that error appears in the above-identified patent and that said Letters Patent are hereby corrected as shown below:

Column 33, line 62, the words "Example 25." should be moved to the left hand margin.
Column 38, line 36, correct "chloroform-ethyl"
Column 42, line 45, change "m, (3H," to --m, 3H,--

Signed and Sealed this

Seventh Day of August 1984

[SEAL]

Attest:

GERALD J. MOSSINGHOFF

Attesting Officer    Commissioner of Patents and Trademarks